(12) United States Patent
Houser

(10) Patent No.: US 8,992,567 B1
(45) Date of Patent: Mar. 31, 2015

(54) COMPRESSIBLE, DEFORMABLE, OR DEFLECTABLE TISSUE CLOSURE DEVICES AND METHOD OF MANUFACTURE

(75) Inventor: Russell A. Houser, Livermore, CA (US)

(73) Assignee: Cardiovascular Technologies Inc., Livermore, CA (US)

( * ) Notice: Subject to any disclaimer, the term of this patent is extended or adjusted under 35 U.S.C. 154(b) by 269 days.

(21) Appl. No.: 12/563,297

(22) Filed: Sep. 21, 2009

Related U.S. Application Data

(63) Continuation of application No. 11/279,242, filed on Apr. 10, 2006, which is a continuation of application No. 10/224,659, filed on Aug. 21, 2002, now Pat. No. 7,025,776, which is a continuation of application No. 10/127,714, filed on Apr. 23, 2002, now abandoned.

(60) Provisional application No. 60/286,269, filed on Apr. 24, 2001, provisional application No. 60/300,892, filed on Jun. 25, 2011, provisional application No. 60/302,255, filed on Jun. 28, 2001.

(51) Int. Cl.
*A61B 17/04* (2006.01)
*A61B 17/08* (2006.01)

(52) U.S. Cl.
CPC ..................... *A61B 17/08* (2013.01)
USPC ....................................... 606/213

(58) Field of Classification Search
USPC ............ 606/95, 108, 109, 213; 604/174, 175, 604/907
See application file for complete search history.

(56) References Cited

U.S. PATENT DOCUMENTS 3,270,745 A   9/1966 Charle
3,459,189 A   8/1969 Alley et al.

(Continued)

FOREIGN PATENT DOCUMENTS

EP   0047618 A1   3/1982
EP   0139 091 A1   5/1985

(Continued)

OTHER PUBLICATIONS

International search report and written opinion dated Jul. 27, 2011 for PCT Application No. US2010/056059.

(Continued)

*Primary Examiner* — Julian W Woo
(74) *Attorney, Agent, or Firm* — Wilson, Sonsini, Goodrich & Rosati; Darby Chan

(57) ABSTRACT

A vascular closure system includes a swellable or bioabsorbable sealing element and a plunger advancement tool. The sealing element and plunger advancement tool is configured to be inserted into the inside of a tubular medical device (such as a vascular introducer sheath, catheter, cannula, trocar, electrode wire, etc.) with the sealing element being advanced distally past the end of the tubular medical device to a desired area within the body (near or at least partially within an arteriotomy, for example) by the plunger. Once in contact with blood (or other fluid) the sealing element may swell, sealing the puncture site. The system may include one of several different features designed to assist the physician to position the sealing element in the desired location. Additional versions of the system described herein can be used for cardiovascular applications where hemostasis (temporary or permanent) is desired. Additionally, the system can be used with simple modifications for any vessel, area on, in or near any vessel, tissue area, tubular structure, duct, organ, hollow body cavity, chamber, tissue wall, or any other structures or tissues, where temporary or permanent sealing, plugging, reduction of flow, reduction of an open space, stabilization or reinforcement is needed. The system is adaptable for use in cardiovascular, gastrointestinal, neurological, reproductive, lymphatic, respiratory, and orthopedic procedures.

31 Claims, 21 Drawing Sheets

(56) References Cited

U.S. PATENT DOCUMENTS

| | | |
|---|---|---|
| 3,675,639 A | 7/1972 | Cimber |
| 3,702,611 A | 11/1972 | Fishbein |
| 3,859,998 A | 1/1975 | Thomas et al. |
| 3,874,388 A | 4/1975 | King et al. |
| 3,937,733 A | 2/1976 | Ulbrich et al. |
| 4,007,743 A | 2/1977 | Blake |
| 4,008,720 A | 2/1977 | Brinckmann et al. |
| 4,052,989 A | 10/1977 | Kline |
| 4,108,175 A | 8/1978 | Orton |
| 4,154,226 A | 5/1979 | Hennig et al. |
| 4,207,870 A | 6/1980 | Eldridge |
| 4,314,555 A | 2/1982 | Sagae |
| 4,317,445 A | 3/1982 | Robinson |
| 4,357,846 A | 11/1982 | Primo |
| 4,394,373 A | 7/1983 | Malette et al. |
| 4,447,915 A * | 5/1984 | Weber ............................ 606/95 |
| 4,468,224 A | 8/1984 | Enzmann et al. |
| 4,487,605 A | 12/1984 | McGaughey et al. |
| 4,525,157 A | 6/1985 | Vaillancourt |
| 4,543,086 A | 9/1985 | Johnson |
| 4,598,711 A | 7/1986 | Deniega |
| 4,610,659 A | 9/1986 | Friese |
| 4,610,671 A | 9/1986 | Luther |
| 4,645,492 A | 2/1987 | Weeks |
| 4,650,488 A | 3/1987 | Bays et al. |
| 4,652,256 A | 3/1987 | Vaillancourt |
| 4,654,031 A | 3/1987 | Lentz |
| 4,655,750 A | 4/1987 | Vaillancourt |
| 4,669,473 A | 6/1987 | Richards et al. |
| 4,710,173 A | 12/1987 | McFarlane |
| 4,738,658 A | 4/1988 | Magro et al. |
| 4,744,364 A | 5/1988 | Kensey |
| 4,770,183 A | 9/1988 | Groman et al. |
| 4,772,264 A | 9/1988 | Cragg |
| 4,774,091 A | 9/1988 | Yamahira et al. |
| 4,787,391 A | 11/1988 | Elefteriades |
| 4,792,326 A | 12/1988 | Tews |
| 4,832,045 A | 5/1989 | Goldberger |
| 4,836,204 A | 6/1989 | Landymore et al. |
| 4,852,568 A | 8/1989 | Kensey |
| 4,863,431 A | 9/1989 | Vailancourt |
| 4,890,612 A | 1/1990 | Kensey |
| 4,894,052 A | 1/1990 | Crawford |
| 4,904,240 A | 2/1990 | Hoover |
| 4,955,890 A | 9/1990 | Yamamoto et al. |
| 4,957,105 A | 9/1990 | Kurth |
| 4,959,048 A * | 9/1990 | Seder et al. .................. 604/907 |
| 4,961,729 A | 10/1990 | Vailancourt |
| 5,021,059 A | 6/1991 | Kensey et al. |
| 5,030,207 A | 7/1991 | Mersch et al. |
| 5,035,701 A | 7/1991 | Kabbara |
| 5,053,008 A | 10/1991 | Bajaj |
| 5,053,046 A | 10/1991 | Janese |
| 5,059,210 A | 10/1991 | Clark et al. |
| 5,061,274 A | 10/1991 | Kensey |
| 5,074,840 A | 12/1991 | Yoon |
| 5,092,841 A | 3/1992 | Spears |
| 5,100,416 A | 3/1992 | Oh et al. |
| 5,108,420 A | 4/1992 | Marks |
| 5,108,421 A | 4/1992 | Fowler |
| 5,116,357 A | 5/1992 | Eberbach |
| 5,120,319 A | 6/1992 | Van Heugten et al. |
| 5,120,527 A | 6/1992 | Li et al. |
| 5,127,626 A | 7/1992 | Hilal et al. |
| 5,128,121 A | 7/1992 | Berg et al. |
| 5,160,339 A | 11/1992 | Chen et al. |
| 5,163,959 A | 11/1992 | Herrick |
| 5,171,270 A * | 12/1992 | Herrick ........................ 604/907 |
| 5,176,653 A | 1/1993 | Metals |
| 5,192,301 A * | 3/1993 | Kamiya et al. ................ 606/213 |
| 5,201,900 A | 4/1993 | Nardella |
| 5,207,691 A | 5/1993 | Nardella |
| 5,209,776 A | 5/1993 | Bass et al. |
| 5,219,353 A | 6/1993 | Garvey et al. |
| 5,222,974 A | 6/1993 | Kensey et al. |
| 5,254,133 A | 10/1993 | Seid |
| 5,269,809 A | 12/1993 | Hayhurst et al. |
| 5,275,616 A | 1/1994 | Fowler |
| 5,283,063 A | 2/1994 | Freeman |
| 5,290,310 A | 3/1994 | Makower et al. |
| 5,292,332 A | 3/1994 | Lee |
| 5,292,362 A | 3/1994 | Bass et al. |
| 5,306,234 A | 4/1994 | Johnson |
| 5,314,410 A | 5/1994 | Marks |
| 5,324,306 A | 6/1994 | Makower et al. |
| 5,330,445 A | 7/1994 | Haaga |
| 5,333,624 A | 8/1994 | Tovey |
| 5,334,137 A | 8/1994 | Freeman |
| 5,334,216 A | 8/1994 | Vidal et al. |
| 5,342,393 A | 8/1994 | Stack |
| 5,350,399 A | 9/1994 | Erlebacher et al. |
| 5,350,404 A | 9/1994 | Adams et al. |
| 5,366,459 A | 11/1994 | Yoon |
| 5,370,650 A | 12/1994 | Tovey et al. |
| 5,376,376 A | 12/1994 | Li |
| 5,382,899 A | 1/1995 | Funatsu et al. |
| 5,383,896 A | 1/1995 | Gershony et al. |
| 5,383,899 A | 1/1995 | Hammerslag |
| RE34,866 E | 2/1995 | Kensey et al. |
| 5,391,183 A | 2/1995 | Janzen et al. |
| 5,405,360 A | 4/1995 | Tovey |
| 5,409,499 A | 4/1995 | Yi |
| 5,417,651 A | 5/1995 | Guena et al. |
| 5,419,760 A | 5/1995 | Narciso |
| 5,419,765 A | 5/1995 | Weldon et al. |
| 5,425,757 A * | 6/1995 | Tiefenbrun et al. ........... 604/907 |
| 5,431,639 A | 7/1995 | Shaw |
| 5,433,729 A | 7/1995 | Adams et al. |
| 5,443,463 A | 8/1995 | Stern et al. |
| 5,443,481 A | 8/1995 | Lee |
| 5,443,500 A | 8/1995 | Sigwart |
| 5,447,502 A | 9/1995 | Haaga |
| 5,449,375 A | 9/1995 | Vidal et al. |
| 5,454,834 A | 10/1995 | Boebel et al. |
| 5,480,388 A | 1/1996 | Zadini et al. |
| 5,486,195 A | 1/1996 | Myers et al. |
| 5,529,577 A | 6/1996 | Hammerslag |
| 5,531,759 A | 7/1996 | Kensey et al. |
| 5,536,251 A | 7/1996 | Evard et al. |
| 5,556,385 A | 9/1996 | Anderson |
| 5,562,617 A | 10/1996 | Finch, Jr. et al. |
| 5,571,181 A | 11/1996 | Li |
| 5,573,518 A | 11/1996 | Haaga |
| 5,584,801 A | 12/1996 | Kuroyanagi et al. |
| 5,591,189 A | 1/1997 | Yoon |
| 5,591,204 A | 1/1997 | Janzen et al. |
| 5,593,422 A | 1/1997 | Muijs Van De Moer et al. |
| 5,601,602 A | 2/1997 | Fowler |
| 5,609,604 A | 3/1997 | Schwemberger et al. |
| 5,613,974 A | 3/1997 | Andreas et al. |
| 5,618,297 A | 4/1997 | Hart et al. |
| 5,620,456 A | 4/1997 | Sauer et al. |
| 5,620,461 A | 4/1997 | Muijs Van De Moer et al. |
| 5,624,454 A | 4/1997 | Palti et al. |
| 5,626,601 A | 5/1997 | Gershony et al. |
| 5,630,833 A | 5/1997 | Katsaros et al. |
| 5,634,936 A * | 6/1997 | Linden et al. ................. 606/213 |
| 5,643,318 A | 7/1997 | Tsukernik et al. |
| 5,643,596 A | 7/1997 | Pruss et al. |
| 5,645,553 A | 7/1997 | Kolesa et al. |
| 5,645,566 A | 7/1997 | Brenneman et al. |
| 5,645,568 A | 7/1997 | Chervitz et al. |
| 5,645,849 A | 7/1997 | Pruss et al. |
| 5,649,959 A | 7/1997 | Hannam et al. |
| 5,653,730 A | 8/1997 | Hammerslag |
| 5,665,106 A | 9/1997 | Hammerslag |
| 5,665,107 A | 9/1997 | Hammerslag |
| 5,690,674 A | 11/1997 | Diaz |
| 5,697,942 A | 12/1997 | Palti |
| 5,702,421 A | 12/1997 | Schneidt |
| 5,713,859 A | 2/1998 | Finch, Jr. et al. |
| 5,716,375 A | 2/1998 | Fowler |
| 5,718,725 A | 2/1998 | Sterman et al. |
| 5,723,005 A | 3/1998 | Herrick |

(56) References Cited

U.S. PATENT DOCUMENTS

| | | |
|---|---|---|
| 5,725,498 A | 3/1998 | Janzen et al. |
| 5,725,551 A | 3/1998 | Myers et al. |
| 5,733,294 A | 3/1998 | Forber et al. |
| 5,741,223 A | 4/1998 | Janzen et al. |
| 5,759,194 A | 6/1998 | Hammerslag |
| 5,766,183 A | 6/1998 | Sauer |
| 5,782,860 A | 7/1998 | Epstein et al. |
| 5,782,861 A | 7/1998 | Cragg et al. |
| 5,792,173 A | 8/1998 | Breen et al. |
| 5,797,944 A | 8/1998 | Nobles et al. |
| 5,797,960 A | 8/1998 | Stevens et al. |
| 5,810,810 A | 9/1998 | Tay et al. |
| 5,810,884 A | 9/1998 | Kim |
| 5,814,066 A | 9/1998 | Spotnitz |
| 5,814,097 A | 9/1998 | Sterman et al. |
| 5,830,130 A | 11/1998 | Janzen et al. |
| 5,830,171 A | 11/1998 | Wallace |
| 5,830,222 A | 11/1998 | Makower |
| 5,843,108 A | 12/1998 | Samuels |
| 5,843,124 A | 12/1998 | Hammerslag |
| 5,861,003 A | 1/1999 | Latson et al. |
| 5,861,004 A | 1/1999 | Kensey et al. |
| 5,865,791 A | 2/1999 | Whayne et al. |
| 5,868,773 A | 2/1999 | Danks et al. |
| 5,868,778 A | 2/1999 | Gershony et al. |
| 5,879,403 A | 3/1999 | Ostiguy et al. |
| 5,885,258 A | 3/1999 | Sachdeva et al. |
| 5,904,703 A | 5/1999 | Gilson |
| 5,906,631 A | 5/1999 | Imran |
| 5,941,897 A | 8/1999 | Myers |
| 5,948,425 A | 9/1999 | Janzen et al. |
| 5,957,952 A | 9/1999 | Gershony et al. |
| 5,964,782 A | 10/1999 | Lafontaine et al. |
| 5,972,034 A | 10/1999 | Hofmann et al. |
| 5,976,174 A | 11/1999 | Ruiz |
| 5,978,704 A | 11/1999 | Ideker et al. |
| 5,978,705 A | 11/1999 | KenKnight et al. |
| 5,979,446 A | 11/1999 | Loy |
| 5,984,917 A | 11/1999 | Fleischman et al. |
| 5,984,950 A | 11/1999 | Cragg et al. |
| 5,997,580 A | 12/1999 | Mastrorio et al. |
| 6,001,110 A | 12/1999 | Adams |
| 6,004,347 A | 12/1999 | McNamara et al. |
| 6,017,359 A | 1/2000 | Gershony et al. |
| 6,024,755 A | 2/2000 | Addis |
| 6,027,470 A | 2/2000 | Mendius |
| 6,042,592 A | 3/2000 | Schmitt |
| 6,042,601 A | 3/2000 | Smith |
| 6,045,569 A | 4/2000 | Kensey et al. |
| 6,045,570 A | 4/2000 | Epstein et al. |
| 6,056,769 A | 5/2000 | Epstein et al. |
| 6,056,770 A | 5/2000 | Epstein et al. |
| 6,063,099 A | 5/2000 | Danks et al. |
| 6,071,281 A | 6/2000 | Burnside et al. |
| 6,071,300 A | 6/2000 | Brenneman et al. |
| 6,079,414 A | 6/2000 | Roth et al. |
| 6,085,119 A | 7/2000 | Scheiner et al. |
| 6,090,130 A | 7/2000 | Nash et al. |
| 6,090,135 A | 7/2000 | Plaia et al. |
| 6,099,506 A | 8/2000 | Macoviak et al. |
| 6,110,184 A | 8/2000 | Weadock |
| 6,113,608 A | 9/2000 | Monroe et al. |
| 6,126,675 A * | 10/2000 | Shchervinsky et al. ........ 606/213 |
| 6,132,438 A | 10/2000 | Fleischman et al. |
| 6,149,684 A | 11/2000 | Herrick |
| 6,152,144 A | 11/2000 | Lesh et al. |
| 6,156,016 A | 12/2000 | Maginot |
| 6,183,496 B1 | 2/2001 | Urbanski |
| 6,193,733 B1 | 2/2001 | Adams |
| 6,197,042 B1 | 3/2001 | Ginn et al. |
| 6,206,893 B1 | 3/2001 | Klein et al. |
| 6,206,907 B1 | 3/2001 | Marino et al. |
| 6,210,366 B1 | 4/2001 | Sanfilippo |
| 6,224,618 B1 | 5/2001 | Gordon |
| 6,224,630 B1 | 5/2001 | Bao et al. |
| 6,231,561 B1 | 5/2001 | Frazier et al. |
| 6,237,605 B1 | 5/2001 | Vaska et al. |
| 6,238,363 B1 | 5/2001 | Kurihashi |
| 6,241,728 B1 | 6/2001 | Gaiser et al. |
| 6,254,562 B1 | 7/2001 | Fouere |
| 6,258,113 B1 | 7/2001 | Adams et al. |
| 6,261,309 B1 | 7/2001 | Urbanski |
| 6,264,673 B1 | 7/2001 | Egnelov et al. |
| 6,277,140 B2 | 8/2001 | Ginn et al. |
| 6,280,477 B1 | 8/2001 | Mastrorio et al. |
| 6,287,323 B1 | 9/2001 | Hammerslag et al. |
| 6,296,657 B1 * | 10/2001 | Brucker ........................ 606/213 |
| 6,306,114 B1 | 10/2001 | Freeman et al. |
| 6,337,995 B1 | 1/2002 | Mower |
| 6,357,443 B1 | 3/2002 | Loy |
| 6,375,662 B1 | 4/2002 | Schmitt |
| 6,375,671 B1 | 4/2002 | Kobayashi et al. |
| 6,379,366 B1 | 4/2002 | Fleischman et al. |
| 6,383,204 B1 | 5/2002 | Ferrera et al. |
| 6,391,048 B1 | 5/2002 | Ginn et al. |
| 6,402,770 B1 | 6/2002 | Jessen |
| 6,423,051 B1 | 7/2002 | Kaplan et al. |
| 6,425,911 B1 | 7/2002 | Akerfeldt et al. |
| 6,436,088 B2 | 8/2002 | Frazier et al. |
| 6,436,119 B1 | 8/2002 | Erb et al. |
| 6,461,364 B1 | 10/2002 | Ginn et al. |
| 6,463,317 B1 | 10/2002 | Kucharczyk et al. |
| 6,464,712 B1 | 10/2002 | Epstein et al. |
| 6,474,340 B1 | 11/2002 | Vaska et al. |
| 6,482,175 B1 | 11/2002 | Walker |
| 6,485,407 B2 | 11/2002 | Alferness et al. |
| 6,488,689 B1 | 12/2002 | Kaplan et al. |
| 6,494,848 B1 | 12/2002 | Sommercorn et al. |
| 6,497,651 B1 | 12/2002 | Kan et al. |
| 6,502,575 B1 | 1/2003 | Jacobs et al. |
| 6,508,828 B1 | 1/2003 | Akerfeldt et al. |
| 6,511,508 B1 | 1/2003 | Shahinpoor et al. |
| 6,517,575 B1 | 2/2003 | Yang et al. |
| 6,537,299 B1 | 3/2003 | Hogendijk et al. |
| 6,546,270 B1 | 4/2003 | Goldin et al. |
| 6,547,806 B1 | 4/2003 | Ding |
| 6,549,812 B1 | 4/2003 | Smits |
| 6,551,303 B1 | 4/2003 | Van Tassel et al. |
| 6,561,969 B2 | 5/2003 | Frazier et al. |
| 6,589,269 B2 | 7/2003 | Zhu et al. |
| 6,596,012 B2 | 7/2003 | Akerfeldt et al. |
| 6,610,026 B2 | 8/2003 | Cragg et al. |
| 6,612,069 B2 | 9/2003 | Locke et al. |
| 6,613,059 B2 | 9/2003 | Schaller et al. |
| 6,623,509 B2 | 9/2003 | Ginn |
| 6,623,510 B2 | 9/2003 | Carley et al. |
| 6,626,918 B1 | 9/2003 | Ginn et al. |
| 6,629,533 B1 | 10/2003 | Webb et al. |
| 6,632,238 B2 | 10/2003 | Ginn et al. |
| 6,632,239 B2 | 10/2003 | Snyder et al. |
| 6,645,205 B2 | 11/2003 | Ginn |
| 6,645,225 B1 * | 11/2003 | Atkinson ...................... 606/213 |
| 6,652,555 B1 | 11/2003 | Van Tassel et al. |
| 6,652,556 B1 | 11/2003 | VanTassel et al. |
| 6,656,207 B2 | 12/2003 | Epstein et al. |
| 6,663,655 B2 | 12/2003 | Ginn et al. |
| 6,666,861 B1 | 12/2003 | Grabek |
| 6,669,687 B1 | 12/2003 | Saadat |
| 6,669,714 B2 | 12/2003 | Coleman et al. |
| 6,679,904 B2 | 1/2004 | Gleeson et al. |
| 6,681,773 B2 | 1/2004 | Murphy et al. |
| 6,682,489 B2 | 1/2004 | Tenerz et al. |
| 6,689,150 B1 | 2/2004 | VanTassel et al. |
| 6,699,240 B2 | 3/2004 | Francischelli |
| 6,702,763 B2 | 3/2004 | Murphy et al. |
| 6,702,835 B2 | 3/2004 | Ginn |
| 6,712,837 B2 | 3/2004 | Akerfeldt et al. |
| 6,716,234 B2 | 4/2004 | Grafton et al. |
| 6,719,777 B2 | 4/2004 | Ginn et al. |
| 6,726,696 B1 | 4/2004 | Houser et al. |
| 6,730,020 B2 | 5/2004 | Peng et al. |
| 6,730,108 B2 | 5/2004 | Van Tassel et al. |
| 6,732,739 B2 | 5/2004 | Cosgrove |
| 6,736,815 B2 | 5/2004 | Ginn |

(56) References Cited

U.S. PATENT DOCUMENTS

| | | | |
|---|---|---|---|
| 6,743,259 B2 | 6/2004 | Ginn | |
| 6,746,461 B2 | 6/2004 | Fry | |
| 6,770,026 B2 | 8/2004 | Kan et al. | |
| 6,776,784 B2 | 8/2004 | Ginn | |
| 6,780,197 B2 | 8/2004 | Roe et al. | |
| 6,786,905 B2 | 9/2004 | Swanson et al. | |
| 6,786,915 B2 | 9/2004 | Akerfeldt et al. | |
| 6,790,218 B2 | 9/2004 | Jayaraman | |
| 6,793,664 B2 | 9/2004 | Mazzocchi et al. | |
| 6,830,576 B2 | 12/2004 | Fleischman et al. | |
| 6,846,319 B2 * | 1/2005 | Ginn et al. | 606/213 |
| 6,860,895 B1 | 3/2005 | Akerfeldt et al. | |
| 6,890,343 B2 | 5/2005 | Ginn et al. | |
| 6,896,692 B2 | 5/2005 | Ginn et al. | |
| 6,941,169 B2 | 9/2005 | Pappu | |
| 6,949,113 B2 | 9/2005 | Van Tassel et al. | |
| 6,959,711 B2 | 11/2005 | Murphy et al. | |
| 6,969,397 B2 | 11/2005 | Ginn | |
| 6,970,742 B2 | 11/2005 | Mann et al. | |
| 6,994,092 B2 | 2/2006 | van der Burg et al. | |
| 6,994,093 B2 | 2/2006 | Murphy et al. | |
| 7,001,398 B2 | 2/2006 | Carley et al. | |
| 7,008,439 B1 | 3/2006 | Janzen et al. | |
| 7,011,671 B2 | 3/2006 | Welch | |
| 7,025,773 B2 | 4/2006 | Gittings et al. | |
| 7,025,776 B1 | 4/2006 | Houser et al. | |
| 7,029,838 B2 | 4/2006 | Williams et al. | |
| 7,044,134 B2 | 5/2006 | Khairkhahan et al. | |
| 7,052,492 B2 | 5/2006 | Swanson et al. | |
| 7,052,829 B2 | 5/2006 | Williams et al. | |
| 7,056,294 B2 | 6/2006 | Khairkhahan et al. | |
| 7,083,614 B2 | 8/2006 | Fjield et al. | |
| 7,083,635 B2 | 8/2006 | Ginn | |
| 7,112,219 B2 | 9/2006 | Vidlund et al. | |
| 7,115,095 B2 | 10/2006 | Eigler et al. | |
| 7,128,073 B1 | 10/2006 | van der Burg et al. | |
| 7,128,740 B2 | 10/2006 | Jacobs et al. | |
| 7,137,953 B2 | 11/2006 | Eigler et al. | |
| 7,144,411 B2 | 12/2006 | Ginn et al. | |
| 7,152,605 B2 | 12/2006 | Khairkhahan et al. | |
| 7,169,164 B2 | 1/2007 | Borillo et al. | |
| 7,182,771 B1 | 2/2007 | Houser et al. | |
| 7,189,199 B2 | 3/2007 | McCarthy et al. | |
| 7,192,439 B2 | 3/2007 | Khairkhahan et al. | |
| 7,211,048 B1 | 5/2007 | Najafi et | |
| 7,217,284 B2 | 5/2007 | Houser et al. | |
| 7,226,458 B2 | 6/2007 | Kaplan et al. | |
| 7,250,057 B2 | 7/2007 | Forsberg | |
| 7,288,090 B2 | 10/2007 | Swanson | |
| 7,293,562 B2 | 11/2007 | Malecki et al. | |
| 7,297,144 B2 | 11/2007 | Fleischman et al. | |
| 7,318,829 B2 | 1/2008 | Kaplan et al. | |
| 7,326,201 B2 | 2/2008 | Fjield et al. | |
| 7,327,862 B2 | 2/2008 | Murphy et al. | |
| 7,335,219 B1 | 2/2008 | Ashby et al. | |
| 7,335,220 B2 | 2/2008 | Khosravi et al. | |
| 7,344,543 B2 | 3/2008 | Sra | |
| 7,344,553 B2 | 3/2008 | Opolski et al. | |
| 7,361,183 B2 | 4/2008 | Ginn | |
| 7,427,279 B2 | 9/2008 | Frazier et al. | |
| 7,429,264 B2 | 9/2008 | Melkent et al. | |
| 7,455,669 B2 | 11/2008 | Swanson | |
| 7,483,743 B2 | 1/2009 | Mann et al. | |
| 7,575,586 B2 | 8/2009 | Berg et al. | |
| 7,931,671 B2 | 4/2011 | Tenerz | |
| 8,105,352 B2 | 1/2012 | EgnelöV | |
| 8,118,831 B2 | 2/2012 | Egnelöv et al. | |
| 8,157,836 B2 * | 4/2012 | Adams | 606/213 |
| 8,518,063 B2 | 8/2013 | Houser et al. | |
| 2001/0003158 A1 | 6/2001 | Kensey et al. | |
| 2001/0003986 A1 | 6/2001 | Cosgrove | |
| 2001/0007077 A1 | 7/2001 | Ginn et al. | |
| 2001/0034509 A1 | 10/2001 | Cragg et al. | |
| 2002/0019648 A1 | 2/2002 | Akerfeldt et al. | |
| 2002/0022860 A1 | 2/2002 | Borillo et al. | |
| 2002/0026208 A1 | 2/2002 | Roe et al. | |
| 2002/0032454 A1 | 3/2002 | Durgin et al. | |
| 2002/0049457 A1 | 4/2002 | Kaplan et al. | |
| 2002/0058925 A1 | 5/2002 | Kaplan et al. | |
| 2002/0065512 A1 | 5/2002 | Fjield et al. | |
| 2002/0072768 A1 | 6/2002 | Ginn | |
| 2002/0077656 A1 | 6/2002 | Ginn et al. | |
| 2002/0077657 A1 | 6/2002 | Ginn et al. | |
| 2002/0077658 A1 | 6/2002 | Ginn | |
| 2002/0082641 A1 | 6/2002 | Ginn et al. | |
| 2002/0087151 A1 | 7/2002 | Mody et al. | |
| 2002/0099390 A1 | 7/2002 | Kaplan et al. | |
| 2002/0103492 A1 | 8/2002 | Kaplan et al. | |
| 2002/0111636 A1 | 8/2002 | Fleischman et al. | |
| 2002/0111637 A1 | 8/2002 | Kaplan et al. | |
| 2002/0111647 A1 | 8/2002 | Khairkhahan et al. | |
| 2002/0128640 A1 | 9/2002 | Swanson | |
| 2002/0133193 A1 | 9/2002 | Ginn et al. | |
| 2002/0133227 A1 | 9/2002 | Murphy et al. | |
| 2002/0147456 A1 | 10/2002 | Diduch et al. | |
| 2002/0147461 A1 | 10/2002 | Aldrich et al. | |
| 2002/0183823 A1 | 12/2002 | Pappu | |
| 2002/0188318 A1 | 12/2002 | Carley et al. | |
| 2003/0023141 A1 | 1/2003 | Stelzer et al. | |
| 2003/0023262 A1 | 1/2003 | Welch | |
| 2003/0023266 A1 | 1/2003 | Borillo et al. | |
| 2003/0023267 A1 | 1/2003 | Ginn | |
| 2003/0032858 A1 | 2/2003 | Ginn et al. | |
| 2003/0045896 A1 | 3/2003 | Murphy et al. | |
| 2003/0050630 A1 | 3/2003 | Mody et al. | |
| 2003/0050632 A1 | 3/2003 | Fjield et al. | |
| 2003/0050659 A1 | 3/2003 | Murphy et al. | |
| 2003/0057156 A1 | 3/2003 | Peterson et al. | |
| 2003/0065339 A1 | 4/2003 | Snyder et al. | |
| 2003/0078598 A1 | 4/2003 | Ginn et al. | |
| 2003/0078616 A1 | 4/2003 | Ginn et al. | |
| 2003/0079753 A1 | 5/2003 | Vaska et al. | |
| 2003/0083542 A1 | 5/2003 | Alferness et al. | |
| 2003/0120337 A1 | 6/2003 | Van Tassel et al. | |
| 2003/0125604 A1 | 7/2003 | Kochamba et al. | |
| 2003/0158464 A1 | 8/2003 | Bertolero | |
| 2003/0163146 A1 | 8/2003 | Epstein et al. | |
| 2003/0178033 A1 | 9/2003 | Cosgrove | |
| 2003/0181901 A1 | 9/2003 | Maguire et al. | |
| 2003/0181940 A1 | 9/2003 | Murphy et al. | |
| 2003/0181942 A1 | 9/2003 | Sutton et al. | |
| 2003/0181945 A1 | 9/2003 | Opolski et al. | |
| 2003/0187362 A1 | 10/2003 | Murphy et al. | |
| 2003/0191462 A1 | 10/2003 | Jacobs et al. | |
| 2003/0191526 A1 | 10/2003 | Van Tassel et al. | |
| 2003/0195560 A1 | 10/2003 | Ginn | |
| 2003/0195561 A1 | 10/2003 | Carley et al. | |
| 2003/0220667 A1 | 11/2003 | van der Burg et al. | |
| 2003/0225443 A1 | 12/2003 | Kiran et al. | |
| 2004/0009289 A1 | 1/2004 | Carley et al. | |
| 2004/0010273 A1 | 1/2004 | Diduch et al. | |
| 2004/0010285 A1 | 1/2004 | Carley et al. | |
| 2004/0030335 A1 | 2/2004 | Zenati et al. | |
| 2004/0034366 A1 | 2/2004 | van der Burg et al. | |
| 2004/0039414 A1 | 2/2004 | Carley et al. | |
| 2004/0044361 A1 | 3/2004 | Frazier et al. | |
| 2004/0049210 A1 | 3/2004 | Van Tassel et al. | |
| 2004/0064014 A1 | 4/2004 | Melvin et al. | |
| 2004/0064138 A1 | 4/2004 | Grabek | |
| 2004/0073241 A1 | 4/2004 | Barry et al. | |
| 2004/0093025 A1 | 5/2004 | Egnelöv | |
| 2004/0098031 A1 | 5/2004 | van der Burg et al. | |
| 2004/0098042 A1 | 5/2004 | Devellian et al. | |
| 2004/0122467 A1 | 6/2004 | VanTassel et al. | |
| 2004/0127935 A1 | 7/2004 | VanTassel et al. | |
| 2004/0127940 A1 | 7/2004 | Ginn et al. | |
| 2004/0147969 A1 | 7/2004 | Mann et al. | |
| 2004/0148019 A1 | 7/2004 | Vidlund et al. | |
| 2004/0158287 A1 | 8/2004 | Cragg et al. | |
| 2004/0167580 A1 | 8/2004 | Mann et al. | |
| 2004/0175522 A1 | 9/2004 | Tajima | |
| 2004/0186486 A1 | 9/2004 | Roue et al. | |
| 2004/0215230 A1 | 10/2004 | Frazier et al. | |
| 2004/0220560 A1 | 11/2004 | Briscoe | |

(56) References Cited

U.S. PATENT DOCUMENTS

| | | |
|---|---|---|
| 2004/0225212 A1 | 11/2004 | Okerlund et al. |
| 2004/0232597 A1 | 11/2004 | Sjostedt et al. |
| 2004/0249342 A1 | 12/2004 | Khosravi et al. |
| 2004/0249412 A1 | 12/2004 | Snow et al. |
| 2004/0267193 A1 | 12/2004 | Bagaoisan et al. |
| 2004/0267307 A1 | 12/2004 | Bagaoisan et al. |
| 2004/0267308 A1 | 12/2004 | Bagaoisan et al. |
| 2005/0004641 A1 | 1/2005 | Pappu |
| 2005/0004652 A1 | 1/2005 | van der Burg et al. |
| 2005/0010252 A1 | 1/2005 | Ideker |
| 2005/0021016 A1 | 1/2005 | Malecki et al. |
| 2005/0033285 A1 | 2/2005 | Swanson et al. |
| 2005/0033287 A1 | 2/2005 | Sra |
| 2005/0033321 A1 | 2/2005 | Fleischman et al. |
| 2005/0038470 A1 | 2/2005 | van der Burg et al. |
| 2005/0049573 A1 | 3/2005 | VanTassel et al. |
| 2005/0049681 A1 | 3/2005 | Greenhalgh et al. |
| 2005/0070952 A1 | 3/2005 | Devellian |
| 2005/0085805 A1 | 4/2005 | Swanson |
| 2005/0085854 A1 | 4/2005 | Ginn |
| 2005/0085856 A1 | 4/2005 | Ginn |
| 2005/0113861 A1 | 5/2005 | Corcoran et al. |
| 2005/0113868 A1 | 5/2005 | Devellian et al. |
| 2005/0119695 A1 | 6/2005 | Carley et al. |
| 2005/0131503 A1 | 6/2005 | Solem |
| 2005/0149068 A1 | 7/2005 | Williams et al. |
| 2005/0149069 A1 | 7/2005 | Bertolero et al. |
| 2005/0149115 A1 | 7/2005 | Roue et al. |
| 2005/0149117 A1 | 7/2005 | Khosravi et al. |
| 2005/0154404 A1 | 7/2005 | Liddicoat et al. |
| 2005/0169974 A1 | 8/2005 | Tenerz et al. |
| 2005/0177180 A1 | 8/2005 | Kaganov et al. |
| 2005/0177182 A1 | 8/2005 | van der Burg et al. |
| 2005/0177183 A1 | 8/2005 | Thorne et al. |
| 2005/0177189 A1 | 8/2005 | Ginn et al. |
| 2005/0197716 A1 | 9/2005 | Sharkey et al. |
| 2005/0203410 A1 | 9/2005 | Jenkins |
| 2005/0203568 A1 | 9/2005 | van der Burg et al. |
| 2005/0222533 A1 | 10/2005 | Chanduszko et al. |
| 2005/0222614 A1 | 10/2005 | Ginn et al. |
| 2005/0234540 A1 | 10/2005 | Peavey et al. |
| 2005/0234543 A1 | 10/2005 | Glaser et al. |
| 2005/0245876 A1 | 11/2005 | Khosravi et al. |
| 2005/0245963 A1 | 11/2005 | Kida et al. |
| 2005/0267521 A1 | 12/2005 | Forsberg |
| 2005/0267528 A1 | 12/2005 | Ginn et al. |
| 2005/0273129 A1 | 12/2005 | Michels et al. |
| 2005/0273137 A1 | 12/2005 | Ginn |
| 2005/0277959 A1 | 12/2005 | Cosgrove et al. |
| 2005/0283187 A1 | 12/2005 | Longson |
| 2006/0004352 A1 | 1/2006 | Vaska et al. |
| 2006/0004388 A1 | 1/2006 | Whayne et al. |
| 2006/0009715 A1 | 1/2006 | Khairkhahan et al. |
| 2006/0009753 A1 | 1/2006 | Fjield et al. |
| 2006/0020162 A1 | 1/2006 | Whayne et al. |
| 2006/0020271 A1 | 1/2006 | Stewart et al. |
| 2006/0034930 A1 | 2/2006 | Khosravi et al. |
| 2006/0047313 A1 | 3/2006 | Khanna et al. |
| 2006/0058844 A1 | 3/2006 | White et al. |
| 2006/0074397 A1 | 4/2006 | Shimada |
| 2006/0074410 A1 | 4/2006 | Malecki et al. |
| 2006/0099238 A1 | 5/2006 | Khosravi et al. |
| 2006/0100664 A1 | 5/2006 | Pai et al. |
| 2006/0106442 A1 | 5/2006 | Richardson et al. |
| 2006/0135989 A1 | 6/2006 | Carley et al. |
| 2006/0136051 A1 | 6/2006 | Furst et al. |
| 2006/0149314 A1 | 7/2006 | Borillo et al. |
| 2006/0167484 A1 | 7/2006 | Carley et al. |
| 2006/0178694 A1 | 8/2006 | Greenhalgh et al. |
| 2006/0190014 A1 | 8/2006 | Ginn et al. |
| 2006/0190037 A1 | 8/2006 | Ginn et al. |
| 2006/0190038 A1 | 8/2006 | Carley et al. |
| 2006/0195123 A1 | 8/2006 | Ginn et al. |
| 2006/0195124 A1 | 8/2006 | Ginn et al. |
| 2006/0206109 A1 | 9/2006 | Swanson |
| 2006/0206121 A1 | 9/2006 | Chin et al. |
| 2006/0206148 A1 | 9/2006 | Khairkhahan et al. |
| 2006/0229672 A1 | 10/2006 | Forsberg |
| 2006/0229674 A1 | 10/2006 | Forsberg |
| 2006/0247672 A1 | 11/2006 | Vidlund et al. |
| 2006/0247680 A1 | 11/2006 | Amplatz et al. |
| 2006/0253037 A1 | 11/2006 | Ginn et al. |
| 2006/0253072 A1 | 11/2006 | Pai et al. |
| 2006/0253129 A1 | 11/2006 | Liddicoat et al. |
| 2006/0263418 A1 | 11/2006 | White |
| 2006/0265007 A1 | 11/2006 | White et al. |
| 2006/0271032 A1 | 11/2006 | Chin et al. |
| 2006/0271089 A1 | 11/2006 | Alejandro et al. |
| 2006/0287661 A1 | 12/2006 | Bolduc et al. |
| 2006/0287674 A1 | 12/2006 | Ginn et al. |
| 2007/0004984 A1 | 1/2007 | Crum et al. |
| 2007/0016228 A1 | 1/2007 | Salas |
| 2007/0032734 A1 | 2/2007 | Najafi et al. |
| 2007/0032823 A1 | 2/2007 | Tegg |
| 2007/0032824 A1 | 2/2007 | Terwey |
| 2007/0043344 A1 | 2/2007 | Mcauley |
| 2007/0060950 A1 | 3/2007 | Khosravi et al. |
| 2007/0060951 A1 | 3/2007 | Shannon |
| 2007/0066993 A1 | 3/2007 | Kreidler |
| 2007/0073313 A1 | 3/2007 | Liddicoat et al. |
| 2007/0073345 A1 | 3/2007 | Pipenhagen et al. |
| 2007/0083227 A1 | 4/2007 | van der Burg et al. |
| 2007/0083230 A1 | 4/2007 | Javois |
| 2007/0123817 A1 | 5/2007 | Khosravi et al. |
| 2007/0129758 A1 | 6/2007 | Saadat |
| 2007/0149988 A1 | 6/2007 | Michler et al. |
| 2007/0156010 A1 | 7/2007 | Aboul-Hosn |
| 2007/0156084 A1 | 7/2007 | Belhe et al. |
| 2007/0156123 A1 | 7/2007 | Moll et al. |
| 2007/0162048 A1 | 7/2007 | Quinn et al. |
| 2007/0179345 A1 | 8/2007 | Santilli |
| 2007/0185530 A1 | 8/2007 | Chin-Chen et al. |
| 2007/0198060 A1 | 8/2007 | Devellian et al. |
| 2007/0208329 A1 | 9/2007 | Ward et al. |
| 2007/0219546 A1 | 9/2007 | Mody et al. |
| 2007/0233226 A1 | 10/2007 | Kochamba et al. |
| 2007/0244476 A1 | 10/2007 | Kochamba et al. |
| 2007/0255314 A1 | 11/2007 | Forsberg |
| 2007/0260278 A1 | 11/2007 | Wheeler et al. |
| 2007/0265641 A1 | 11/2007 | Roue et al. |
| 2007/0270891 A1 | 11/2007 | Mcguckin |
| 2007/0276433 A1 | 11/2007 | Huss |
| 2007/0287999 A1 | 12/2007 | Malecki et al. |
| 2008/0004658 A1 | 1/2008 | Malecki et al. |
| 2008/0009843 A1 | 1/2008 | de la Torre |
| 2008/0015569 A1 | 1/2008 | Saadat et al. |
| 2008/0033241 A1 | 2/2008 | Peh et al. |
| 2008/0033457 A1 | 2/2008 | Francischelli et al. |
| 2008/0039879 A1 | 2/2008 | Chin et al. |
| 2008/0045946 A1 | 2/2008 | Vaska |
| 2008/0058862 A1 | 3/2008 | Khosravi et al. |
| 2008/0058864 A1 | 3/2008 | Bagaoisan et al. |
| 2008/0071311 A1 | 3/2008 | White et al. |
| 2008/0082122 A1 | 4/2008 | Khosravi et al. |
| 2008/0097488 A1 | 4/2008 | Fleischman et al. |
| 2008/0097521 A1 | 4/2008 | Khosravi et al. |
| 2008/0109030 A1 | 5/2008 | Houser et al. |
| 2008/0114394 A1 | 5/2008 | Houser et al. |
| 2008/0125795 A1 | 5/2008 | Kaplan et al. |
| 2008/0125848 A1 | 5/2008 | Kusleika et al. |
| 2008/0132602 A1 | 6/2008 | Rizk et al. |
| 2008/0147097 A1 | 6/2008 | Liddicoat et al. |
| 2008/0167713 A1 | 7/2008 | Bolling |
| 2008/0167750 A1 | 7/2008 | Stahler et al. |
| 2008/0221593 A1 | 9/2008 | Liddicoat et al. |
| 2008/0243111 A1 | 10/2008 | Gammie et al. |
| 2008/0243183 A1 | 10/2008 | Miller et al. |
| 2008/0249397 A1 | 10/2008 | Kapadia |
| 2008/0269801 A1 | 10/2008 | Coleman et al. |
| 2008/0269802 A1 | 10/2008 | Coleman et al. |
| 2008/0272173 A1 | 11/2008 | Coleman et al. |
| 2008/0294088 A1 | 11/2008 | Solem et al. |
| 2008/0294175 A1 | 11/2008 | Bardsley et al. |
| 2008/0312664 A1 | 12/2008 | Bardsley et al. |

(56) References Cited

U.S. PATENT DOCUMENTS

| | | |
|---|---|---|
| 2008/0312676 A1 | 12/2008 | Solem |
| 2009/0005674 A1 | 1/2009 | Saadat et al. |
| 2009/0005777 A1 | 1/2009 | Houser et al. |
| 2009/0012354 A1 | 1/2009 | Wood |
| 2009/0012545 A1 | 1/2009 | Williamson, IV et al. |
| 2009/0088793 A1 | 4/2009 | Bagaoisan et al. |
| 2009/0112257 A1 | 4/2009 | Preinitz et al. |
| 2009/0143789 A1 | 6/2009 | Houser et al. |
| 2009/0143808 A1 | 6/2009 | Houser et al. |
| 2009/0254121 A1 | 10/2009 | Newth et al. |
| 2010/0312259 A1 | 12/2010 | Houser et al. |
| 2011/0144661 A1 | 6/2011 | Houser et al. |
| 2014/0081318 A1 | 3/2014 | Houser et al. |

FOREIGN PATENT DOCUMENTS

| | | |
|---|---|---|
| EP | 0401525 A1 | 12/1990 |
| JP | 2007-516731 A | 6/2007 |
| SU | 782814 | 11/1980 |
| SU | 1088709 | 4/1984 |
| WO | WO 90/01497 A1 | 2/1990 |
| WO | WO 91/15155 A1 | 10/1991 |
| WO | WO 01/97696 A1 | 12/2001 |
| WO | WO 03/096881 A2 | 11/2003 |
| WO | WO 03/096881 A3 | 4/2004 |

OTHER PUBLICATIONS

International search report and written opinion dated Mar. 8, 2011 for PCT Application No. US2010/030531.
International Search Report dated Jul. 12, 2004 for PCT/US2004/040933.
Office action dated Jan. 22, 2013 for U.S. Appl. No. 12/563,320.
Office action dated Feb. 7, 2005 for U.S. Appl. No. 10/224,659.
Office action dated Mar. 15, 2012 for U.S. Appl. No. 12/561,104.
Office action dated Mar. 17, 2008 for U.S. Appl. No. 11/279,242.
Office action dated Apr. 6, 2009 for U.S. Appl. No. 11/279,242.
Office action dated Apr. 13, 2011 for U.S. Appl. No. 12/263,322.
Office action dated Apr. 14, 2011 for U.S. Appl. No. 10/831,850.
Office action dated Apr. 19, 2012 for U.S. Appl. No. 12/563,371.
Office action dated May 2, 2007 for U.S. Appl. No. 11/279,242.
Office action dated May 15, 2007 for U.S. Appl. No. 10/785,486.
Office action dated Jun. 18, 2012 for U.S. Appl. No. 12/563,320.
Office action dated Jun. 19, 2012 for U.S. Appl. No. 11/930,111.
Office action dated Jul. 22, 2005 for U.S. Appl. No. 10/224,659.
Office action dated Jul. 26, 2012 for U.S. Appl. No. 12/167,212.
Office action dated Sep. 13, 2006 for U.S. Appl. No. 10/785,486.
Office action dated Sep. 23, 2011 for U.S. Appl. No. 11/933,129.
Office action dated Oct. 15, 2008 for U.S. Appl. No. 10/785,486.
Office action dated Nov. 13, 2008 for U.S. Appl. No. 11/279,242.
Office action dated Nov. 23, 2011 for U.S. Appl. No. 12/263,322.
Office action dated Nov. 29, 2011 for U.S. Appl. No. 12/327,655.
Office action dated Dec. 12, 2007 for U.S. Appl. No. 10/785,486.
U.S. Appl. No. 13/786,375, filed Mar. 5, 2013, Houser et al.
Office action dated Mar. 28, 2013 for U.S. Appl. No. 12/757,275.
Office action dated Mar. 29, 2013 for U.S. Appl. No. 12/942,914.
Office action dated Jun. 24, 2013 for U.S. Appl. No. 12/757,275.
Office action dated Aug. 14, 2013 for U.S. Appl. No. 11/279,242.
Notice of allowance dated May 23, 2013 for U.S. Appl. No. 12/167,212.
Notice of allowance dated Oct. 16, 2014 for U.S. Appl. No. 12/263,322.
Notice of allowance dated Nov. 4, 2005 for U.S. Appl. No. 10/224,659.
Office action dated Jan. 10, 2014 for U.S. Appl. No. 12/263,322.
Office action dated Oct. 22, 2013 for U.S. Appl. No. 12/563,338.
Office action dated Nov. 19, 2013 for U.S. Appl. No. 12/942,914.

* cited by examiner

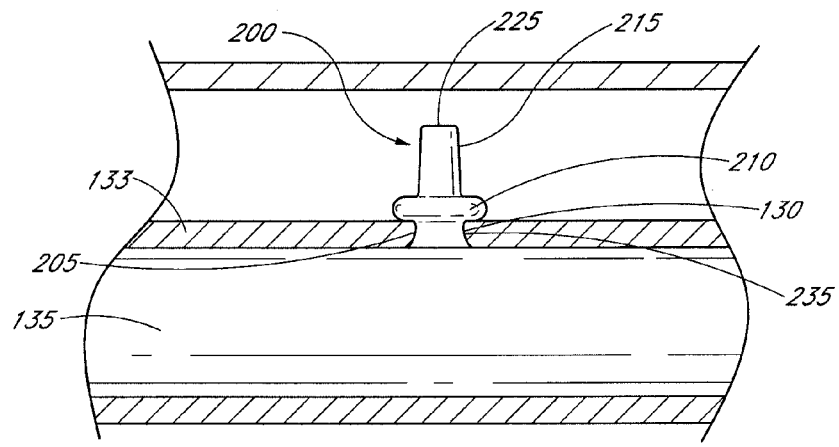
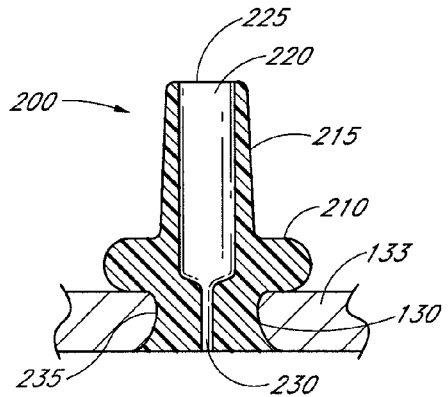
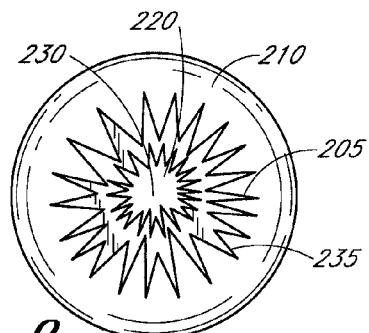
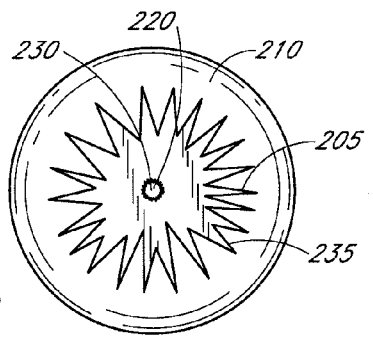
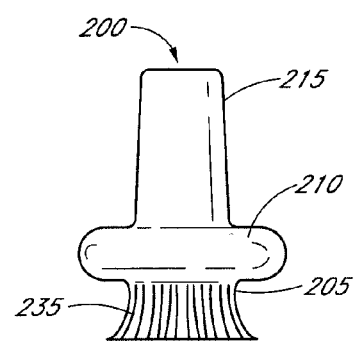
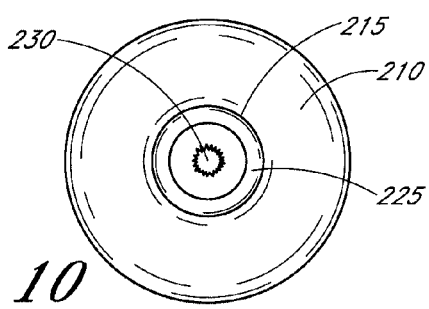

COMPRESSIBLE, DEFORMABLE, OR DEFLECTABLE TISSUE CLOSURE DEVICES AND METHOD OF MANUFACTURE

RELATED APPLICATIONS

This application is a continuation of U.S. patent application Ser. No. 11/279,242 filed Apr. 10, 2006, entitled "Arteriotomy Closure Devices and Techniques," currently pending, which is a continuation of U.S. patent application Ser. No. 10/224,659 filed Aug. 21, 2002, which issued into U.S. Pat. No. 7,025,776 on Apr. 11, 2006, entitled "Arteriotomy Closure Devices and Techniques," which in turn is a continuation of U.S. patent application Ser. No. 10/127,714 filed Apr. 23, 2002, now abandoned, entitled "Arteriotomy Closure Devices and Techniques," to which priority is claimed under 35 U.S.C. §120 and which in turn claims the benefit of U.S. Provisional Patent Application Nos. 60/286,269, filed Apr. 24, 2001, entitled "Percutaneous Vessel Access Closure Device and Method," 60/300,892, filed Jun. 25, 2001, entitled "Percutaneous Vessel Access Closure Device and Method," and from 60/302,255, filed Jun. 28, 2001, entitled "Percutaneous Vessel Access Closure Device and Method (Hemostatic Patch or Collar)," each of which are incorporated herein in their entirety by reference.

TECHNICAL FIELD

The field of the inventions generally relates to cardiovascular and arterial closure devices, and, more particularly, to arterial closure devices and techniques.

BACKGROUND

In most cardiology and radiology procedures, a catheter is inserted into an artery, such as the femoral artery, through a vascular introducer. When the procedure is complete, the physician removes the catheter from the introducer and then removes the introducer from the arteriotomy into the vessel. The physician then must prevent or limit the amount of blood that leaks through the arteriotomy so that the patient can be discharged. Physicians currently use a number of methods to close the arteriotomy, such as localized compression, sutures, collagen plugs, and adhesives, gels, foams, and similar materials. To use localized compression, the physician presses down against the vessel to allow the arteriotomy to naturally clot. This method, however, can take half an hour or more, and requires the patient to remain immobilized for at least that period of time and be kept in the hospital for observation. There are potentials for clots at puncture site to be dislodged. Moreover, the amount of time necessary for the compression can be significantly increased depending upon how much heparin, glycoprotein IIb/IIA antagonists, or other anti-clotting agents were used during the procedure. Sutures and collagen plugs may have procedure variability, may require time to close the vessel, may have negative cost factors, and may necessitate a separate deployment device. Adhesives, gels, and foams may have negative cost factors, may necessitate a possibly complicated deployment process, and may have procedure variability.

SUMMARY

In one general aspect, an arterial closure device is deliverable over a tube for placement within and against an arteriotomy. The arterial closure device includes a first member forming an enlargement around the circumference of the arterial closure device and being configured to be received against an outer surface of a vessel; a connecting member having a smaller outer diameter than the first member, extending from the first member, and being configured to be positioned within an arteriotomy of a vessel; and a longitudinal channel configured to receive a tube and passing between the first member and the connecting member.

Embodiments of the arterial closure device may include one or more of the following features. For example, the connecting member may include slits. The connecting member may be expandable from a first narrow diameter to a second expanded diameter.

The arterial closure device may further include a second member extending from the connecting member, forming an enlargement around the circumference of the arterial closure device and being configured to be received against an inner surface of the vessel when the first member is received against the outer surface of the vessel. The arterial closure device may still further include an adhesive layer on at least one of the first member, the second member, and the connecting member. The first member may extend at an angle from the arterial closure device, the second member may extend at an angle from the arterial closure device, and the first member may be generally oriented in the direction of the second member.

The first member may include at least one superelastic/shape memory element configured to move between a first extended position and a second extended position and the second member may include at least one superelastic/shape memory element configured to move between a first extended position and a second extended position.

The arterial closure device may further include an adhesive layer on at least one of the first member and the connecting member. The arterial closure device may further include an adhesive within the longitudinal channel. The arterial closure device may further include longitudinal slots along the longitudinal channel.

The arterial closure device may further include an extending member extending from the first member in a generally opposite direction away from the connecting member and the longitudinal channel continues from the first member through the extending member. The extending member may include a closable opening of the longitudinal channel. The arterial closure device may further include a slot along at least a part of the length of the arterial closure device.

The arterial closure device may further include a deployment tool, the deployment tool including a handle, a contacting section, and an extension that extends between the handle and the contacting section. The contacting section is configured to mate with the arterial closure device to advance the arterial closure device over the tube and deploy the arterial closure device within the vessel.

In another general aspect, an arterial closure system includes an arterial closure device and a deployment tool. The arterial closure device includes a first member forming an enlargement around the circumference of the arterial closure device and being configured to be received against an outer surface of a vessel, a connecting member having a smaller outer diameter than the first member, extending from the first member, and being configured to be positioned within an arteriotomy of a vessel, and a longitudinal channel configured to receive a tube and passing between the first member and the connecting member. The deployment tool includes a handle, a contacting section, and an extension that extends between the handle and the contacting section, the contacting section being configured to mate with the arterial closure device to advance the arterial closure device over the tube and deploy the arterial closure device within the vessel.

Embodiments of the arterial closure system may include any of the features described above or herein. For example, the arterial closure system may further include a second member extending from the connecting member, forming an enlargement around the circumference of the arterial closure device and being configured to be received against an inner surface of the vessel when the first member is received against the outer surface of the vessel. The first member may include at least one superelastic/shape memory element configured to move between a first extended position and a second extended position; and the second member may include at least one superelastic/shape memory element configured to move between a first extended position and a second extended position.

The arterial closure device may include a slot along at least a portion of the length of the arterial closure device and the contacting section of the deployment tool may include a longitudinal slot.

In another general aspect, a method of closing an opening in a vessel includes providing an arterial closure device that includes a first member forming an enlargement around the circumference of the arterial closure device and being configured to be received against an outer surface of a vessel, a connecting member having a smaller outer diameter than the first member, extending from the first member, and being configured to be positioned within an arteriotomy of a vessel, and a longitudinal channel configured to receive a tube and passing between the first member and the connecting member. The method further includes providing a deployment tool comprising a handle, a contacting section, and an extension that extends between the handle and the contacting section, the contacting section being configured to mate with the arterial closure device to advance the arterial closure device over the tube and deploy the arterial closure device within the vessel. The method still further includes slidably mounting the arterial closure device to a tube; inserting the tube through an opening into the vessel; using the deployment tool to advance and deploy the arterial closure device by advancing the arterial closure device along the tube until the connecting member is deployed within the vessel and the first member is received against the outer surface of the vessel; and removing the tube from the vessel and from the arterial closure device.

Embodiments of the method of closing an opening in a vessel may include any of the features described above or herein. For example the arterial closure device may further include a second member extending from the connecting member, forming an enlargement around the circumference of the arterial closure device and being configured to be received against an inner surface of the vessel when the first member is received against the outer surface of the vessel and an adhesive layer is positioned on at least one of the first member, the second member, and the connecting member, and deploying the arterial closure device further comprises positioning the second member against the inner surface of the vessel.

The arterial closure device, the arterial closure system, and the arterial closure method provides considerable advantages, as described herein. For example, the ACDs and methods described herein can provide: (1) the ability to deploy an ACD without the removal and re-insertion of a second device; (2) the ability to be used on most commercial vascular introducers, catheters, tubes, etc.; (3) the ability to use tactile feedback to correctly and properly deploy an ACD without direct or indirect visual assistance; (4) the ability to use adhesives to secure the device to the vessel; (5) the ability to use adhesives to close off the device to prevent blood leaking or seepage; and (6) the ability to provide eluting therapeutic agents incorporated within or on the device. Moreover, the device, system and method are advantageously simple to use, inexpensive, and effective as a percutaneous vessel access closure device and method.

DESCRIPTION OF THE DRAWINGS

FIGS. 6 and 7 are side and cross-sectional side views, respectively, of a second implementation of an arterial closure device deployed within an arteriotomy of a vessel wall.

FIG. 8 is a bottom end view of the arterial closure device of FIG. 6 showing the flared end opened.

FIG. 9 is a bottom end view of the arterial closure device of FIG. 6 showing the flared end closed.

FIG. 10 is a top end view of the arterial closure device of FIG. 6 showing the flared end partially closed.

FIG. 11 is a side view of the arterial closure device of FIG. 6 showing the flared end.

DETAILED DESCRIPTION

Figure 1:
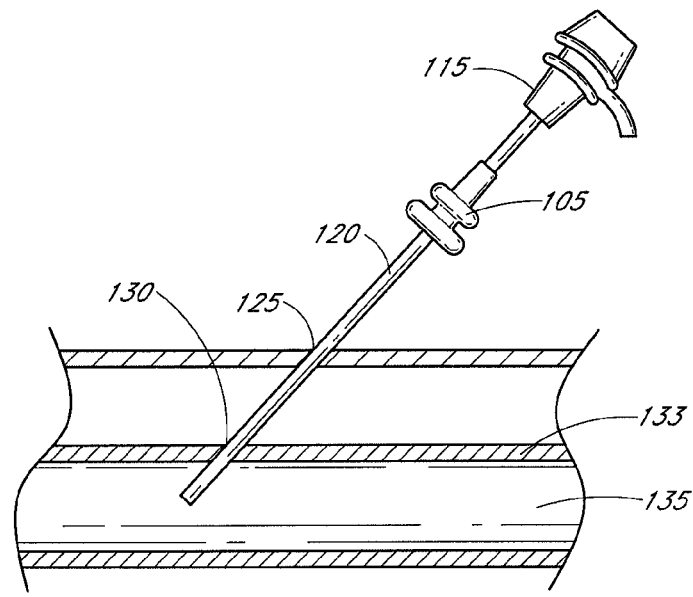
FIG. 1 is a side view of a arterial closure device positioned around a tubular section of a vascular introducer.
Figure 2:
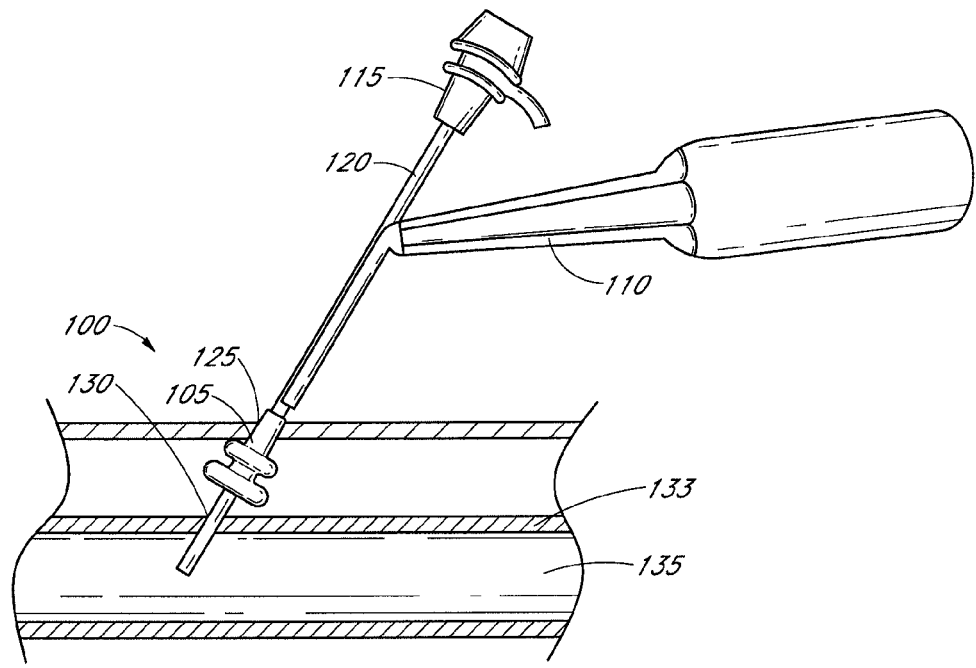
FIG. 2 is a side view of the arterial closure device of FIG. 1 advanced through a percutaneous opening by a deployment instrument.
Figure 3:
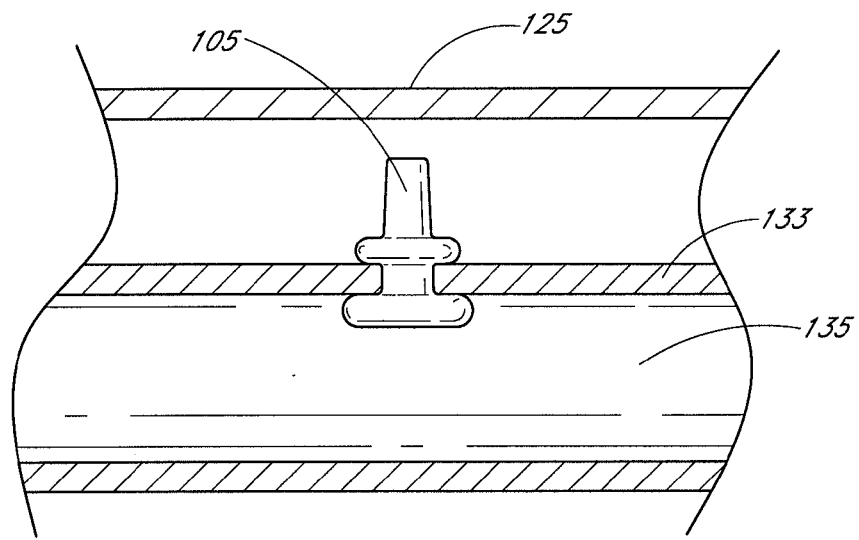
FIG. 3 is a side view of the arterial closure device of FIG. 1 deployed through a vessel wall.

Referring to FIGS. 1-3, a vascular closure system 100 generally includes two components: an arterial closure device ("ACD") 105 and a deployment instrument 110. The ACD 105 is slidably mounted to a vascular introducer 115 or other tubular device, such as a catheter, advanced over a tube section 120 of the introducer 115 using the deployment instrument 110, passed through a percutaneous opening 125, and placed through an arteriotomy 130 in a vessel wall 133 into a blood vessel 135. The deployment tool 110 and the introducer 115 then are removed from the blood vessel 135 and out of the percutaneous opening 125.

Figure 4:
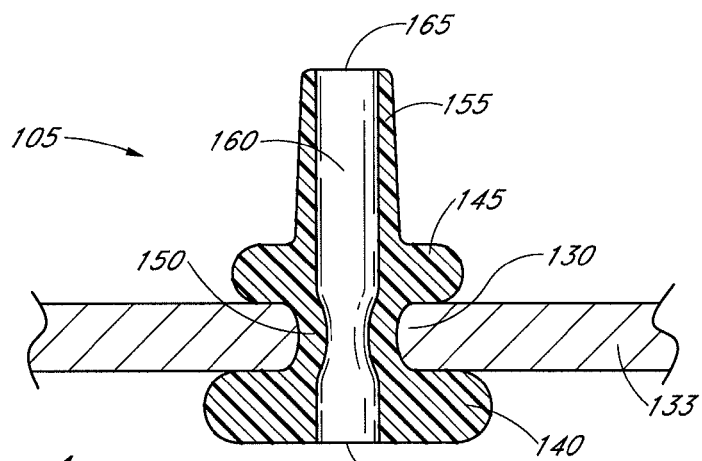
FIG. 4 is a cross-sectional side view of the arterial closure device of FIG. 1 deployed through a vessel wall.
Figure 5:
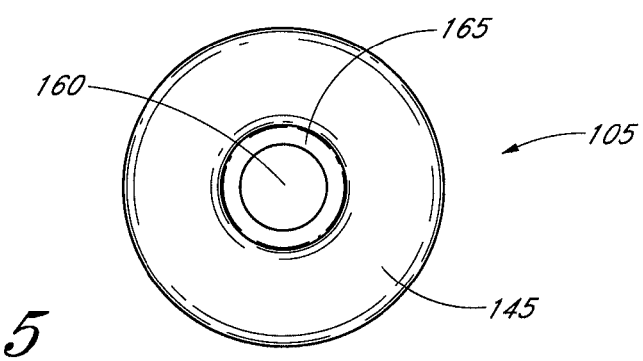
FIG. 5 is a top view of the arterial closure device of FIG. 1.

Referring to FIGS. 4 and 5, the ACD 105 is generally compliant, tubular, and includes a first member 140, a second member 145, a connecting member 150 between the first member and the second member, and an optional extending member 155 that extends from the second member. A longitudinal channel 160 passes between a first opening 165 in the extending member (or second member if the extending member is not present) and a second opening 170 in the first member 140.

The ACD 105 is formed of a tubular structure of sufficient length and thickness (e.g., a single wall thickness of between 0.005" and 0.05", and more particularly between 0.01" and 0.02") that can be advanced over the introducer 115, and through the puncture site 125. The ACD 105 has sufficient rigidity to be advanced through the puncture site 125 yet is compliant enough to be compressed onto itself by the natural elasticity of the vessel wall 133 after the introducer 115 is removed. Moreover, the connecting member 150 can be configured to have a natural elasticity such that when it is no longer mounted over the introducer tube 120, it will return to its original smaller diameter state. The ACD 105 may include, for example, longitudinal sections of the tube where the wall thickness is thinner (e.g., connecting member 150) thereby creating creases or weakened areas that receive the vessel wall 133. The creases would reduce the amount of compressive force required to collapse the tube onto itself. A design allowing tactile feedback may be used to determine the proper insertion position (depth). The tactile feedback could be accomplished by the ACD 105 having one or more rings of increased wall thickness, an "hour glass" geometry, a thin, narrow, then wide geometry, combination, or other means to provide an abrupt change in the advancing force resistance during deployment. The ACD 105 may be manufactured in many different French sizes, to match the outer diameter of any commercial vascular introducers 115.

The ACD 105 is placed around the outside of any commercially available introducer 115, or other device that is inserted into the cardiovascular system (e.g., catheter, etc.), and positioned adjacent to the proximal end of the introducer (i.e., near the valve or luer fitting of the introducer). The introducer 115 then is inserted into the vasculature using standard techniques. Prior to removing the introducer 115, the tubular ACD 115 is advanced to the skin, for example, by the physician manually advancing the ACD along the tube 120. The deployment instrument 110 then is positioned against or clipped onto the tube 120, advanced to be in contact with the proximal end (i.e., second member 145) of the ACD 105, and advanced through the skin such that at least the distal most portion (e.g., first member 140) of the ACD is inside the vessel 135. The ACD 105 is prevented from deforming or collapsing during insertion by the rigidity of the tube 120. The tube 120 also acts as a guide to position the ACD 105 through the puncture site 125 during its advancement and deployment. When the introducer 115 is removed, the deployment instrument 110 is held in position and still in contact with the ACD 105 preventing the ACD from coming out of the vessel 135 along with the introducer. Once the introducer 115 is completely removed, the ACD 105 is compressed together due to the elastic recovery of the vessel wall 133, achieving hemostasis and effectively sealing the arteriotomy 150 and puncture site 125.

The ACD 105 can be partially or completely fabricated from a biocompatible material, such as expanded polytetrafluoroethylene (ePTFE), polyester, polyurethane, silicone, Dacron, urethane, and/or a composite or combination of these or other suitable materials. The ACD 105 also can be partially or completely fabricated from a biodegradable/bioabsorbable material, including modified cellulose, collagen, fibrin, fibrinogen, elastin or other connective proteins or natural materials, polymers or copolymers such as polylactide [poly-L-lactide (PLLA), poly-D-lactide (PDLA)], polyglycolide, polydioxanone, polycaprolactone, polygluconate, polylactic acid (PLA), polylactic acid-polyethylene oxide copolymers, poly(hydroxybutyrate), polyanhydride, polyphosphoester, poly(amino acids), poly(alpha-hydroxy acid) or related copolymers of these materials as well as composites and combinations thereof and combinations of other biodegradable/bioabsorbable materials.

The ACD 105 also can be partially or completely fabricated from materials that swell, or expand when they are exposed to a fluid, such as blood, or another fluid, for example, that can be added by the physician to cause the material to swell. These materials include hydrophilic gels (hydrogels), regenerated cellulose, polyethylene vinyl acetate (PEVA), as well as composites and combinations thereof and combinations of other biocompatible swellable or expandable materials.

The ACD 105 can be made using several methods and processes including extrusion, molding (i.e., injection molding or other known molding techniques), casting, dip coating, spraying, adhesive bonding, ultra-sonic welding, composite fabrication techniques, and combinations of these and/or other similar methods and processes.

The ACD 105 also can have a biocompatible contact adhesive or other material within the longitudinal channel 160 so that when the longitudinal channel is compressed within the arteriotomy 130, the adhesive bonds the inside surfaces of the longitudinal channel together. This assists or expedites the sealing of the arteriotomy. Additionally, bonding materials can be used on the outside of the ACD 105, for example, on the outer surface of the first member 140, the second member 145, the connecting member 150, and or the optional extending member 155. In particular, the bonding material is especially useful where the ACD contacts the vessel wall 133 defining the arteriotomy 130.

The biocompatible contact adhesive adhesive/bonding compounds/solutions could be added during the manufacturing process, just prior to deployment, or after the device has been deployed. The bonding materials could be in the form of a liquid, semi solid, or solid. Suitable bonding materials include gels, foams and microporous mesh. Suitable adhesives include acrylates, cyanoacrylates, epoxies, fibrin-based adhesives, other biological based adhesives, UV light and/or heat activated or other specialized adhesives. The adhesive could bond on initial contact, or longer, to allow repositioning if desired. The preferred adhesive may be a crystalline polymer that changes from a non-tacky crystalline state to an adhesive gel state when the temperature is raised from room temperature to body temperature. Such material is available under the trade name Intillemer™ adhesive, available from Landec Corp. as well as composites and combinations thereof and combinations of other materials. Suppliers of biocompatible adhesives include, but are not limited to, Plasto (Dijon, France), Haemacure (Montreal, Canada), Cohesion (Palo Alto, Calif.), Cryolife (Kennesaw, Ga.), TissueLink (Dover, N.H.), and others. To increase the work time of the adhesive or allow repositioning of the vascular coupler after it has been deployed, the adhesive can be blended with a material, such as a starch or other material, that retards or delays bonding to allow repositioning of the coupler after it has been deployed. A degradable coating can be placed over the adhesive coating so that it degrades and exposes the adhesive. Other adhesives are understood to include composites-based adherents and combinations of the above materials and other suitable materials as are known in the art.

To improve later detection of the ACD 105, it can be fabricated from materials that include one or more radiopaque materials, such as barium sulfate, bismuth trioxide, or other any other radiopaque material. The radiopaque material is added to the materials from which the ACD 105 is fabricated or to the bonding materials that are placed in, on, or around the ACD.

Referring to FIGS. 6-11, a second implementation of a arterial closure device is shown as a arterial closure device ("ACD") 200. The ACD 200 includes a first member 205, a second member 210, and an optional extending member 215 that extends from the second member. A longitudinal channel 220 passes between a first opening 225 in the extending member (or second member if the extending member is not present) and a second opening 230 in the first member 205. The ACD 200 is implanted within an arteriotomy 130 in a manner similar to the implantation of the ACD 105. However, the ACD 200 does not include a member that is substantially in contact with the inner wall of the vessel 135. Instead, the ACD has a flare, or two or more short slits 235 in the side wall of the first member 205. The flare or slits 235 are designed to open or flare around the catheter or introducer 120 when advanced to the top of the vessel puncture site (FIG. 8). The materials from which the ACD 200 or the second member 205 are fabricated may be a very elastic material such that when around the introducer it expands and when advanced beyond the end of the introducer, it contracts such that the individual flares pinch or otherwise catch the edges of the arteriotomy or punctured vessel and pull them together while contracting (FIG. 9). This action is intended to close the arteriotomy 130 and create hemostasis. The inside of the flared section 235 of the ACD 200 may have a biocompatible contact adhesive or other bonding material, as described above, that further secures the ACD within the arteriotomy and to the vessel 135, and, in particular the second member 210 to the top or outer surface of the vessel.

Figure 12:
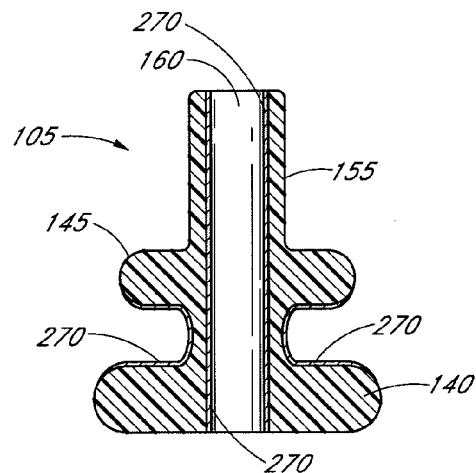
FIGS. 12 and 13 are a cross-sectional side view and a top view, respectively, of the arterial closure device of FIG. 1 having an adhesive on the inner diameter and tissue engagement areas.
Figure 13:
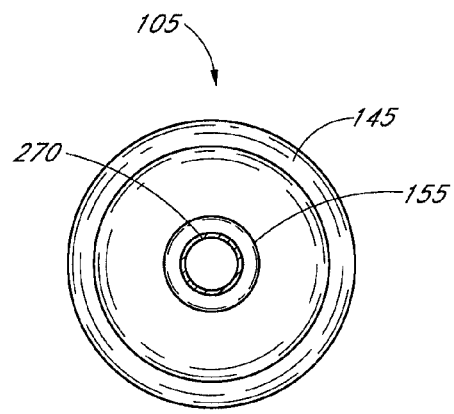
Figure 14:
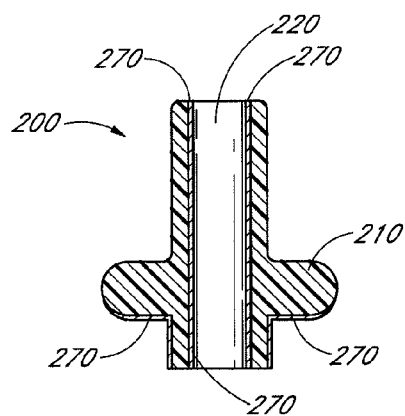
FIGS. 14 and 15 are a cross-sectional side view and a top view, respectively, of the arterial closure device of FIG. 6 having an adhesive on the inner diameter and tissue engagement areas.
Figure 15:
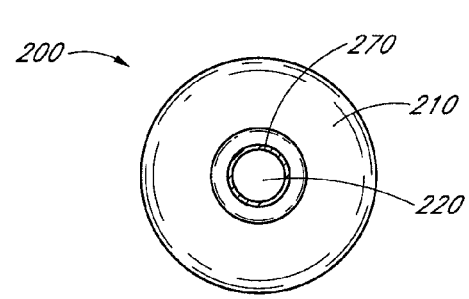

As indicated above, the adhesive or bonding materials can be implemented on any of the above ACDs. For example, referring to FIGS. 12 and 13, the ACD 105 has an adhesive or bonding material 270 on the inner diameter and tissue engagement areas. Similarly, referring to FIGS. 14 and 15, the ACD 200 has the adhesive or bonding material 270 on the inner diameter and tissue engagement areas. In this manner, adhesive 270 will close the respective longitudinal channel 160, 200 of the ACD 105, 200 to reduce or eliminate seepage blood. Moreover, the adhesive 270 around the tissue contacting areas will bond the ACD to the vessel wall to reduce or eliminate seepage of blood through those regions.

Figure 16:
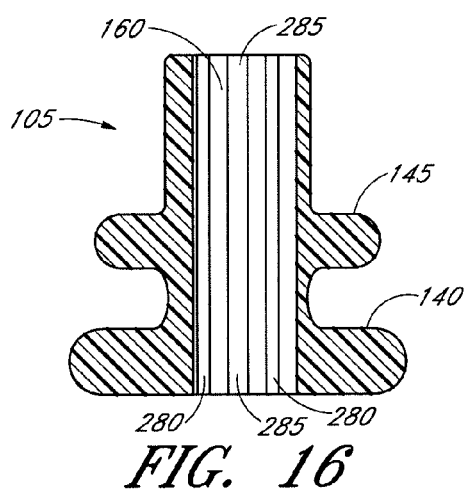
FIGS. 16 and 17 are a cross-sectional side view and a top view, respectively, of the arterial closure device of FIG. 1 having grooves on the inner diameter to form a thinned or weakened wall.
Figure 17:
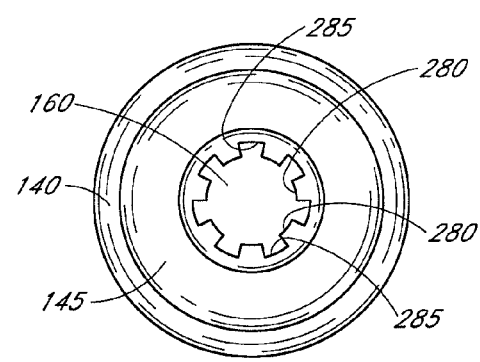

Referring to FIGS. 16 and 17, the ACD 105 can have the inner diameter of the longitudinal channel 160 modified to include ridges 280 and channels 285 that weaken or thin the wall section of the ACD. In this manner, the inner diameter of the longitudinal channel 160 can be expanded or reduced depending upon the circumferential pressure exerted against the ACD. For example, when passing the introducer through the longitudinal channel the inner diameter will be expanded. When the introducer is subsequently removed, the inner diameter is reduced because of the natural elastic recoil properties of the ACD. In this manner, the seepage of blood through the longitudinal channel is reduced or eliminated. Moreover, the surfaces of the inner diameter of the longitudinal channel can be coated with an adhesive, as described above, to further ensure that the inner diameter is closed.

The ACDs described herein also can include one or more therapeutic agents that affect healing at the site where the device is deployed. The agent(s) can be incorporated into the structure forming the device and/or incorporated into a coating. Such therapeutic agents may include, but are not limited to, antithrombotics (such as anticoagulants), antimitogens, antimitotoxins, antisense oligonucleotides, gene therapy solutions, nitric oxide, and growth factors and inhibitors. Direct thrombin inhibitors that may be beneficial include Hirudin, Hirugen, Hirulog, PPACK (D-phenylalanyl-L-propyl-Larginine chloromethyl ketone), Argatreban, and D-FPRCH.sub.2 Cl (D-phenylalanyl-Lpropyl-L-arginyl chloromethyl ketone); indirect thrombin inhibitors include Heparin and Warfarin (coumadin). Alternatively, a clot promoter may be used, such as protamine sulphate or calcium hydroxide. Additional therapeutic materials include, aspirin, dexamethasone, dexamethasone phosphate, streptokinase, tocopherol, TPA, urokinase, paclitaxel (Taxol), actinomycin, rapamyacin, or other. Sirolimus, or other antibiotics may also be used. The therapeutic compounds/solutions may be blended with the device base materials during fabrication, applied just prior to deployment, or after the device has been deployed. Additionally, the therapeutic materials may be located on, through, inside, or combination of the device in holes, grooves, slots or other indentation to allow elution of the therapeutic compound(s). Post device fabrication coating methods include, but are not limited to, dipping, spraying, brushing, submerging the devices into a beaker containing a therapeutic solution while inside a vacuum chamber to permeate the device material, etc.

Figure 18:
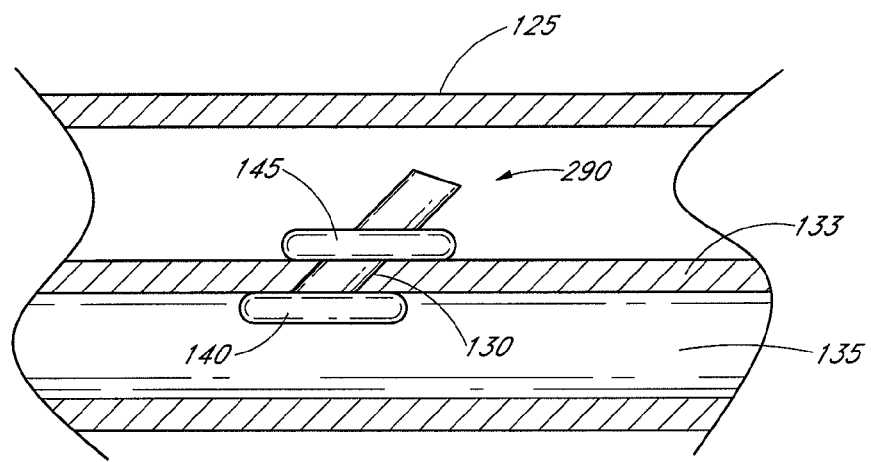
FIG. 18 is a side view of an angled arterial closure device.
Figure 19:
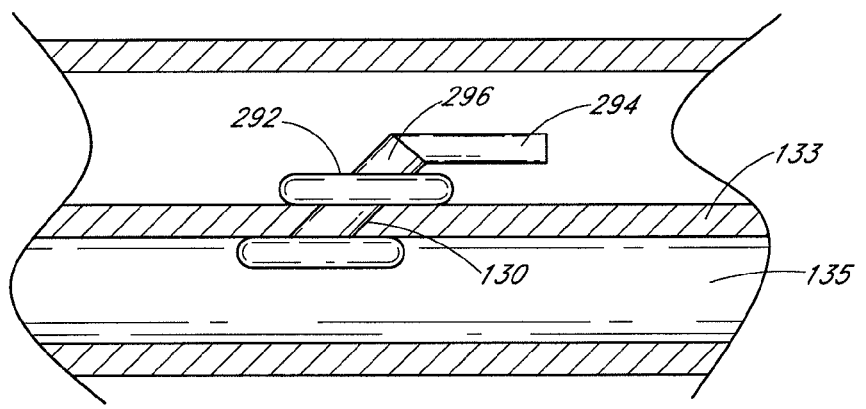
FIG. 19 is a side view of an angled arterial closure device having a foldable extending member.

The geometry of the ACDs described herein is shown for illustration purposes as being generally round. However, they can be of any other geometry, such as oval, elliptical, rectangular, square, ridged, or a combination of shapes. The ACD has been illustrated as forming a generally perpendicular angle with the vessel wall once deployed. Nonetheless, the inventors intend the configuration to be at any suitable angle, such as between 30° and 60°, or, for example, 45° or as otherwise desired. A range of angles of the ACD can be available and the physician can choose the appropriate ACD based on the angle at which the introducer is introduced into the vessel. For example, referring to FIG. 18, an ACD 290 is formed to have the extending member 155 extending at an angle of approximately 45° from the second member 145. In addition, the first member 140 and the second member 145 are longitudinally offset. This configuration is designed to cause the extending member 155 to follow the path created by the introducer. Referring also to FIG. 19, the ACD has a second member 292, a foldable extending member 294, and a groove 296 positioned between the second member 292 and the folding extending member 294. In this manner, the extending member 294 can be folded or bent over to be less obtrusive and to close off the flow of blood through the ACD.

Figure 20:
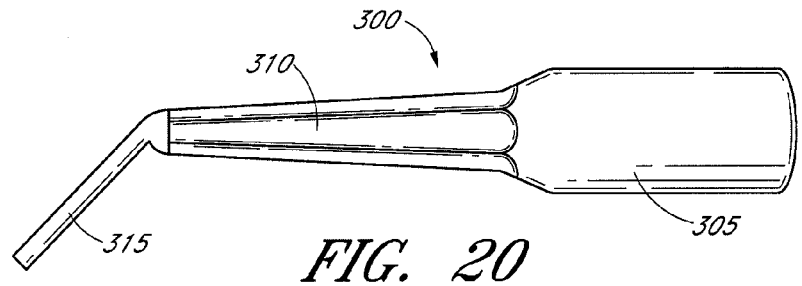
FIG. 20 is a side view of a deployment tool.
Figure 22:
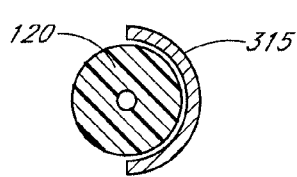
FIG. 22 is an end view of the deployment tool FIG. 20.
Figure 21:
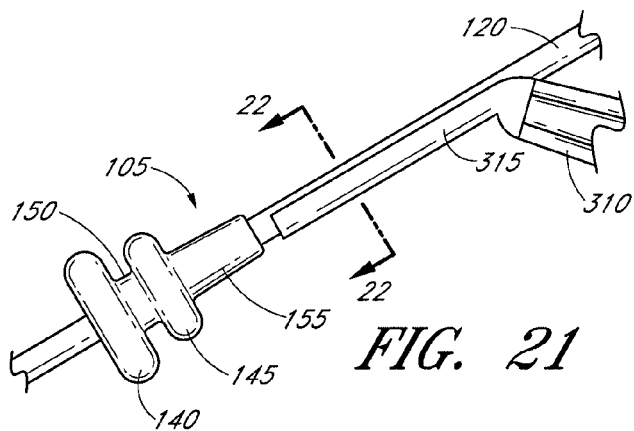
FIG. 21 is a side view of the deployment tool of FIG. 20 used to deploy a arterial closure device.
Figure 23:
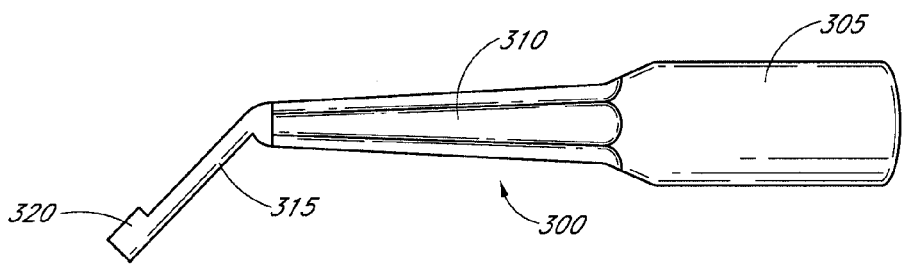
FIG. 23 is a side view of the deployment tool of FIG. 20 having an extended contacting member.
Figure 25:
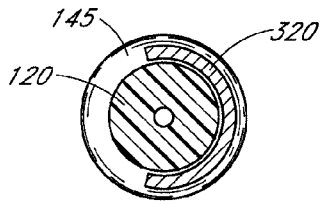
FIG. 25 is an end view of the deployment tool FIG. 23.
Figure 24:
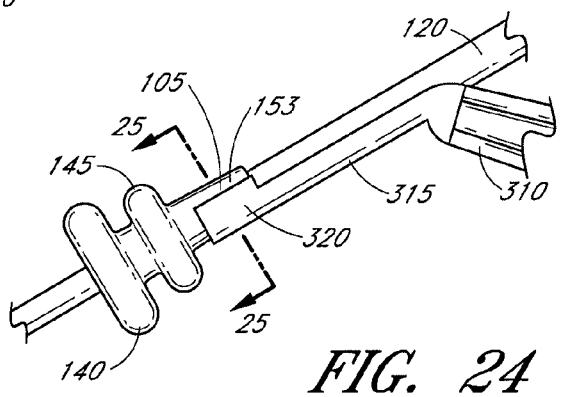
FIG. 24 is a side view of the deployment tool of FIG. 23 used to deploy a arterial closure device.
Figures 26, 27:
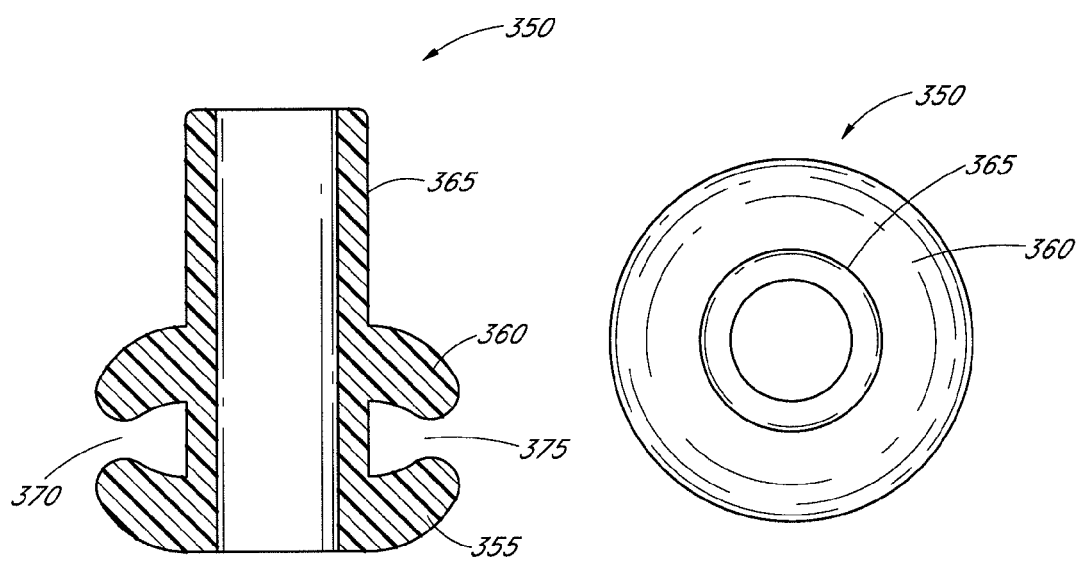
FIG. 26 is a cross-sectional side view of a arterial closure device having angled closure edges for compressing a vessel wall.
FIG. 27 is a top view of the arterial closure device of FIG. 26.

Referring to FIGS. 20-22, a deployment tool 300 is designed to engage or otherwise contact the proximal edge, or other edge, of the ACD. The tool 300 is generally handheld and includes a handle 305, an extension 310, and a contacting section 315 that clips onto, or otherwise contacts the outside of the introducer and mates with the ACD. The contacting section 315 has sufficient length to advance the ACD through the tissue to the desired position on the vessel. The handle 305 or grasping section can be, for example, round, rectangular, elliptical, or a combination of shapes or other shape that fit comfortably in the hand. The contacting section 315 can have a cross-sectional geometry of a partially open tube having more than 50% diameter coverage, so that it can clip onto, and slide over the outer diameter of the introducer.

Referring also to FIGS. 23-35, the deployment tool can include an additional extension 320 that is configured to fit around the extending member 155 and mate with the second member 145. The extension 320 can be attached to the introducer after the introducer is positioned within the artery.

The deployment tool 300 can be made partially or completely from several different polymer materials including polycarbonate, nylon, polyethylene, polytetrafluoroethylene (PTFE), fluoroethylene-propylene (FEP) or polyfluoroacrylate (PFA), polyester ether ketone (PEEK), polyamide, polyimide, polyethyleneteraphthalate (PET), combination or other material able to withstand sterilization processing. The tool can also be made partially or completely from several different types of metals including stainless steel; spring metal alloys such as Elgiloy™, Inconel™; superelastic/shape memory alloys such as Nitinol (NiTi) as well as composites and combinations thereof and combinations of other materials.

The deployment tool 300 can be made using several methods and processes including extrusion, molding (injection and other), casting, adhesive bonding, ultrasonic welding as well as combinations thereof and combinations of other methods and processes.

Modifications of the deployment tool 300 are possible. For example, the proximal edge of the ACD (i.e., of the extending member 155 or the second member 145) and the distal edge or other portion of the advancement tool 300 may have interlocking geometries to aid and/or control the position of the ACD during advancement along the introducer. The engagement/contact section 315, 320 of the tool 300 may have a cross-sectional geometry of a complete circle that is designed to split away from the introducer once the ACD has been advanced and deployed. Splitting can be accomplished by having weakened areas in the wall of the tubing, such as linear perforations, or linear scores. This version would require that the deployment tool be back loaded onto the introducer before the ACD is placed onto the introducer and prior to insertion into the vessel.

The inside, concave section of the contact section 315, 320 may be coated with a hydrophilic or other lubricious material to reduce the friction during advancement and deployment of the ACD. In addition to the deployment tool 300 contacting the proximal edge of the ACD, the contacting section 315, 320 of the tool can be lengthened and designed to further attach to and compress the distal edge of the ACD, thereby providing additional support during insertion and deployment into the vessel.

Figure 28:
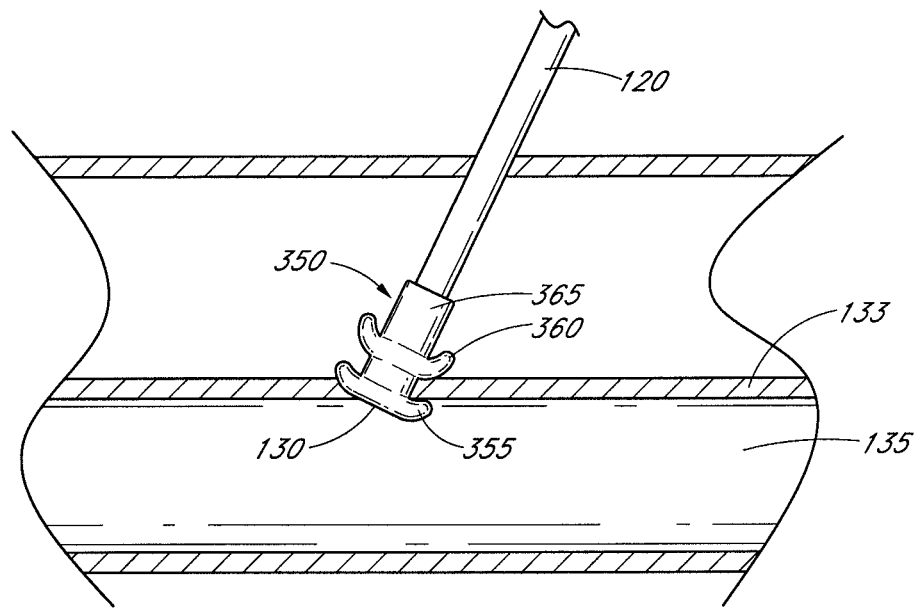
FIG. 28 is a side view of the arterial closure device of FIG. 26 being advanced through the skin into a vessel with the closure edges deflected.
Figure 29:
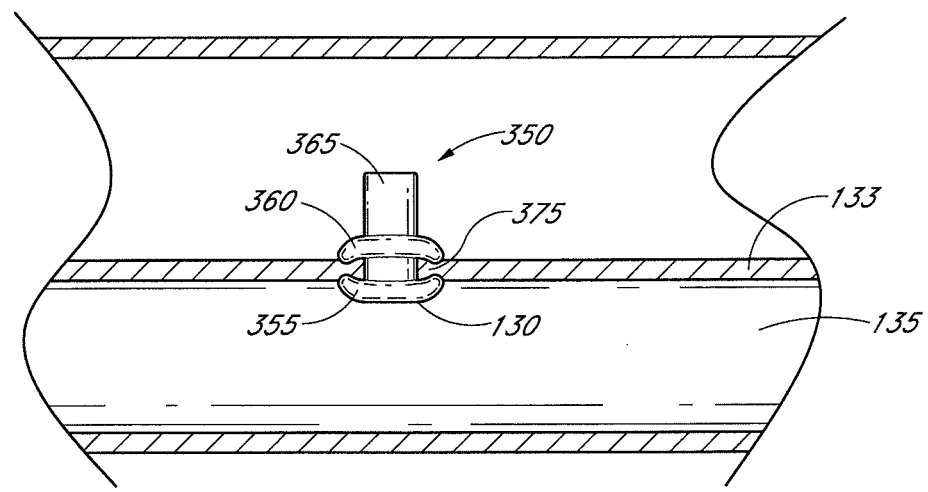
FIG. 29 is a side view of the arterial closure device of FIG. 26 deployed and secured onto vessel wall with the closure edges occluding the arteriotomy.

Referring to FIGS. 26-29, a ACD 350 includes a first angled closure edge 355, a second angled closure edge 360, an extending member 365, and a connection member 370 between the first and second angled closure members. The first angled closure edge 355 and the second angled closure edge are generally directed at each other such that they define a narrow opening 375 through which the vessel wall 133 is received. The ACD 350 is deployed over the introducer tube section 120 using, for example, the deployment tool 300. As illustrated in FIG. 28, the second angled closure edge 360 is deflected away from the first angled closure edge 355. The deflection can be caused, for example, by the contacting section 320 surrounding the second angled closure edge 360. In this manner, when the deployment tool 300 is removed, the second angled closure edge 360 deflects back to compress the vessel wall 133 between the angled closure edges 355, 360. The angled closure edges 355 and 360 are formed, for example, from a flexible member, such as a polymer, superelastic/shape memory material, or a combination of the two. For example, the superelastic/shape memory member can be coated with a polymer.

Figures 30, 31:
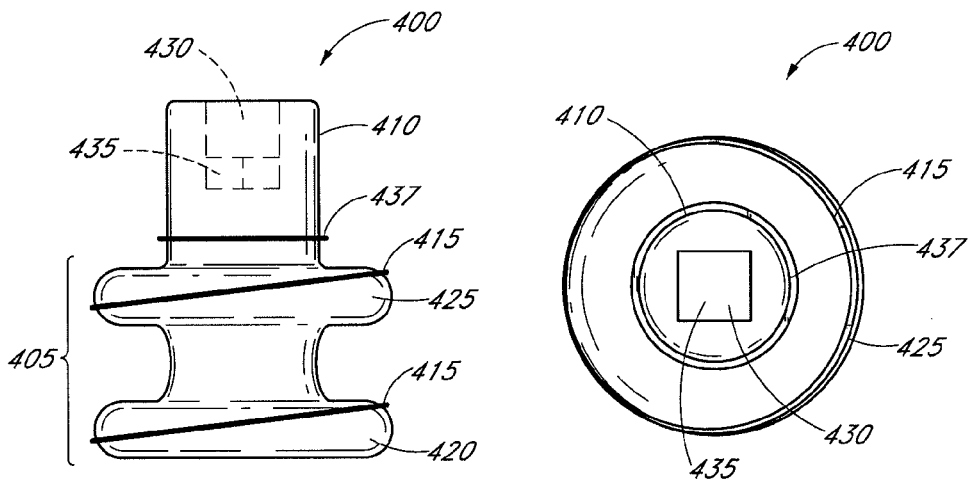
FIG. 30 is a side view of a arterial closure device.
FIG. 31 is an end view of the arterial closure device of FIG. 30.

Referring to FIGS. 30 and 31, a ACD 400 includes a threaded section 405 and an extending section 410. The threaded section 405 includes threads 415 mounted on and between a first member 420 and a second member 425. The extending section 410 includes a longitudinal channel 430 that includes a distal shaped channel 435. A deployment tool having a mating shaped distal end is inserted into the longitudinal channel 430 such that it mates with the distal shaped channel 435. By rotating the deployment tool, the ACD can be threadably inserted into the arteriotomy.

In general, the distal edge of the ACD 400 is designed to engage the opening of the arteriotomy or puncture site and protrude to a specific depth based on how many times the ACD was advanced, twisted or turned. The ACD 400 may have a stop 437 to limit how far the device protrudes into the vessel. The same "screw" type distal edge could be used on a hemostatic plug, made from a solid piece of material, rather than a tube structure. A deployment tool would be needed that has, for example, a grasping distal end for insertion into the vessel.

The ACD 400 can be modified to include a longitudinal channel that pass through the entire length of the device and deployed over a introducer. In this case, the deployment tool and the proximal edge of the ACD would have a mating geometry such that the deployment tool is rotated to threadably insert the ACD through the arteriotomy.

Figure 32:
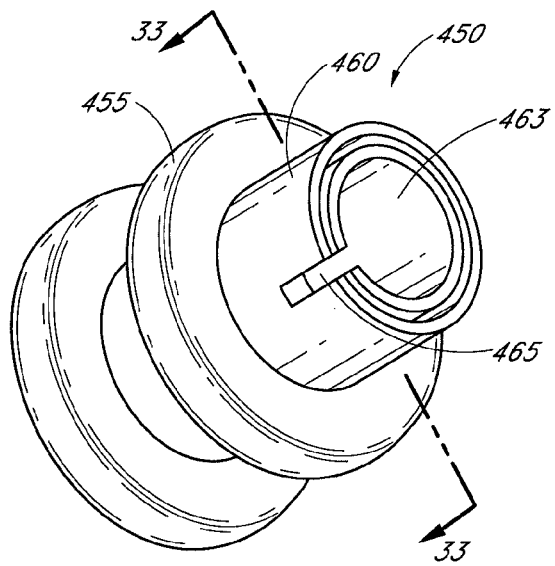
FIG. 32 is a perspective side view of a vascular connector having a closable end.
Figure 33:
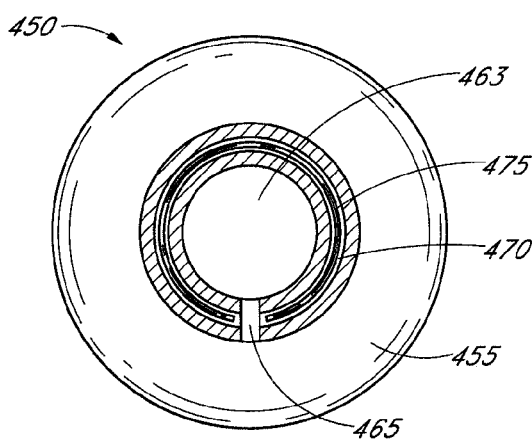
FIG. 33 is an end view of the arterial closure device of FIG. 32.

Referring to FIGS. 32 and 33, a ACD 450 includes a tissue contacting member 455 and an extending member 460. A longitudinal channel 463 passes through the ACD. The extending member 460 includes a longitudinal slot 465 and a circumferential channel 470 in which a contracting member 475 is received. The contracting member 475 tends to close the longitudinal channel 463 unless kept open, for example, by an introducer 115 within the channel. In this manner, when the ACD 450 is deployed within the arteriotomy and the introducer is removed, the longitudinal channel is closed, which prevents or limits blood flow or seepage through the channel. The ACD can be formed from any of the materials described above. For example, the ACD can be formed from a polymer and the extending member can be formed from a flexible material such as a polyurethane/Dacron composite that easily collapses as a consequence of contraction property of the contracting member 475.

Figures 34, 35:
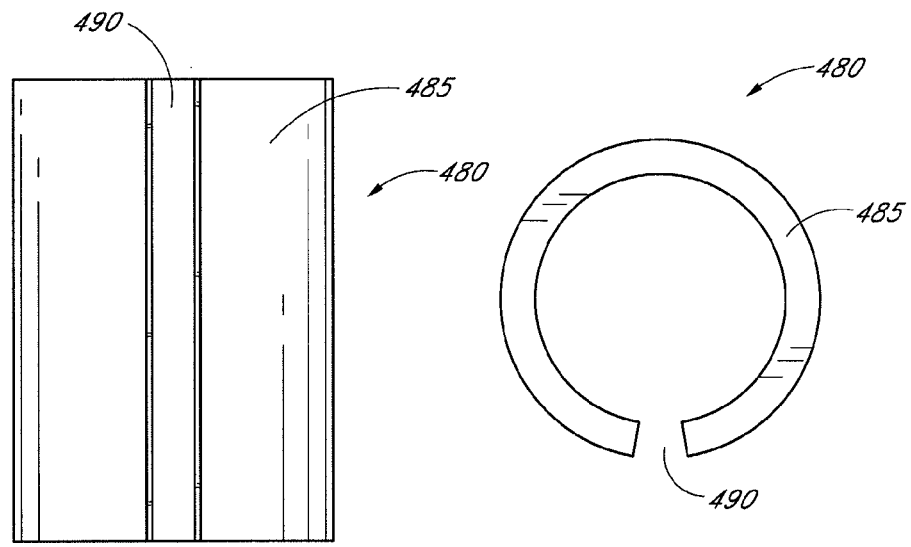
FIG. 34 is a side view of a liner having a longitudinal slot for a arterial closure device.
FIG. 35 is an end view of the liner of FIG. 34.

Referring to FIGS. 34 and 35, a ACD inner liner 480 is formed as a simple slotted tube 485 that includes a slot 490 along its length that functions a means for side access onto the introducer, after the introducer has been inserted into the vessel. The slot 490 can be formed as a longitudinal or radial slit, illustrated below. The ACD inner liner can be opened sufficiently to attach onto the introducer from the side. Any configuration of the ACDs described herein is built around the ACD liner 480 with a slot formed within the ACD. The tube 485 optionally can extend from the ACD and then be clamped at the proximal end once the ACD liner 480 and ACD are deployed.

Figures 36, 37:
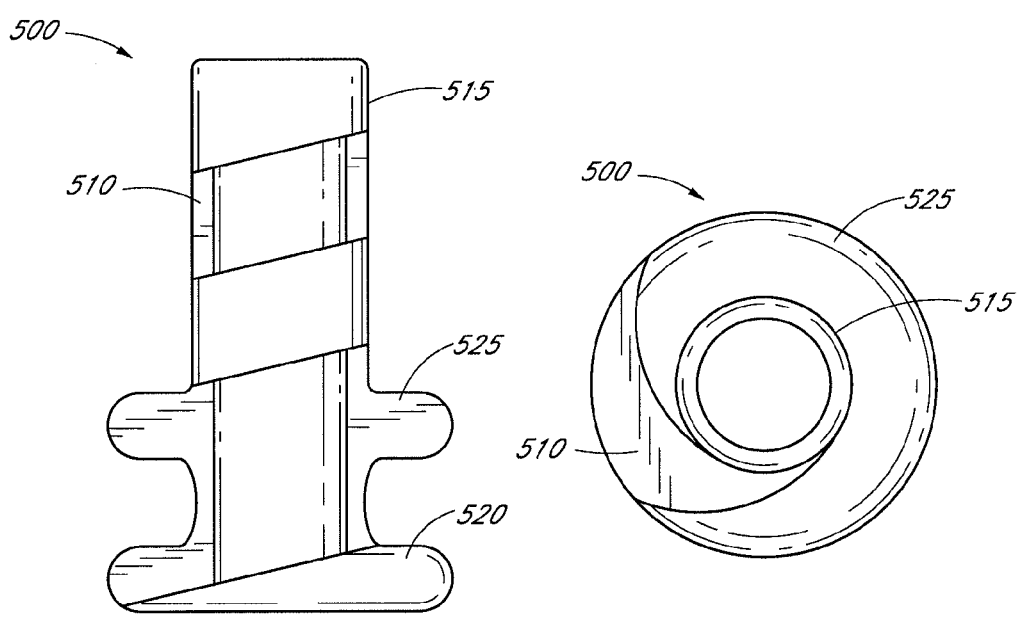
FIG. 36 is a side view of a liner having a radial slot.
FIG. 37 is an end view of the liner of FIG. 36.
Figure 38:
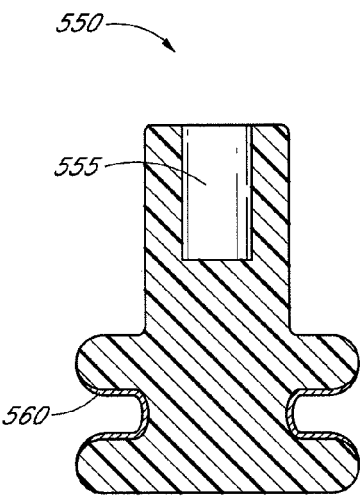
FIG. 38 is a side view of a plug-style arterial closure device that includes an adhesive layer on the vessel contact areas.
Figure 39:
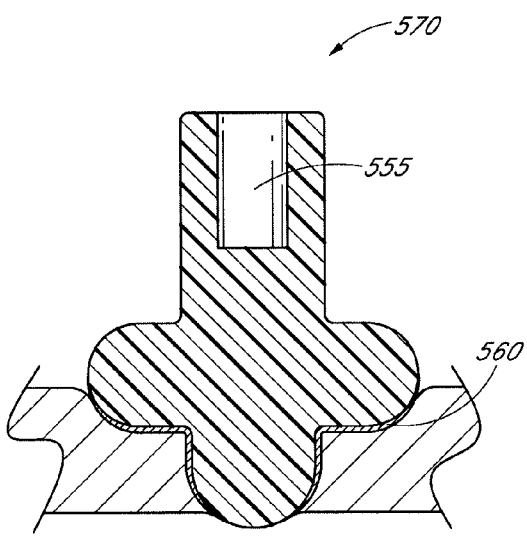
FIG. 39 is a side view of a plug style arterial closure device that has limited vessel protrusion and includes an adhesive on the vessel contacting areas.
Figures 40, 41:
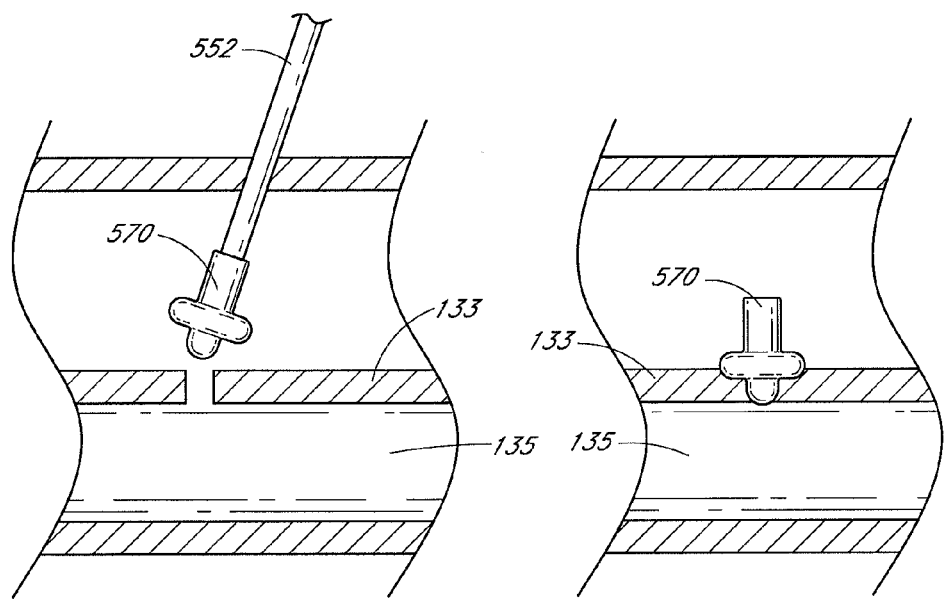
FIGS. 40 and 41 are side views of the plug style arterial closure device of FIG. 39 being deployed and deployed within a vessel.
Figure 42:
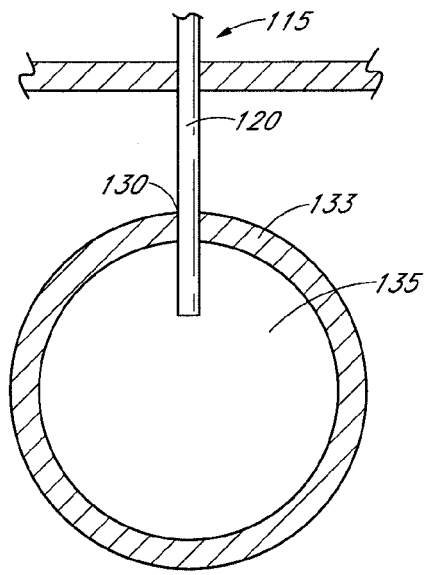
FIG. 42 is an end view showing the distal end of the introducer inside a vessel.
Figure 44:
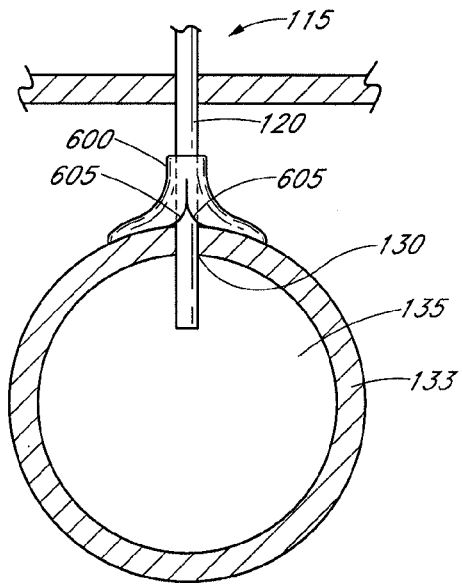
FIGS. 43 and 44 are end views showing a flared arterial closure device deployed along the introducer.
Figure 45:
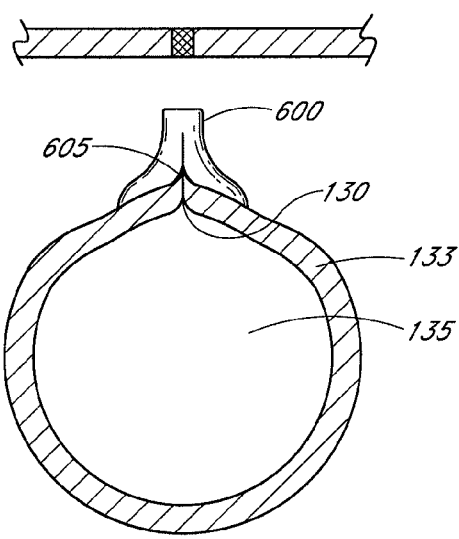
FIG. 45 is an end view showing the flared arterial closure device of FIG. 43 deployed against the vessel to close the arteriotomy.
Figure 43:
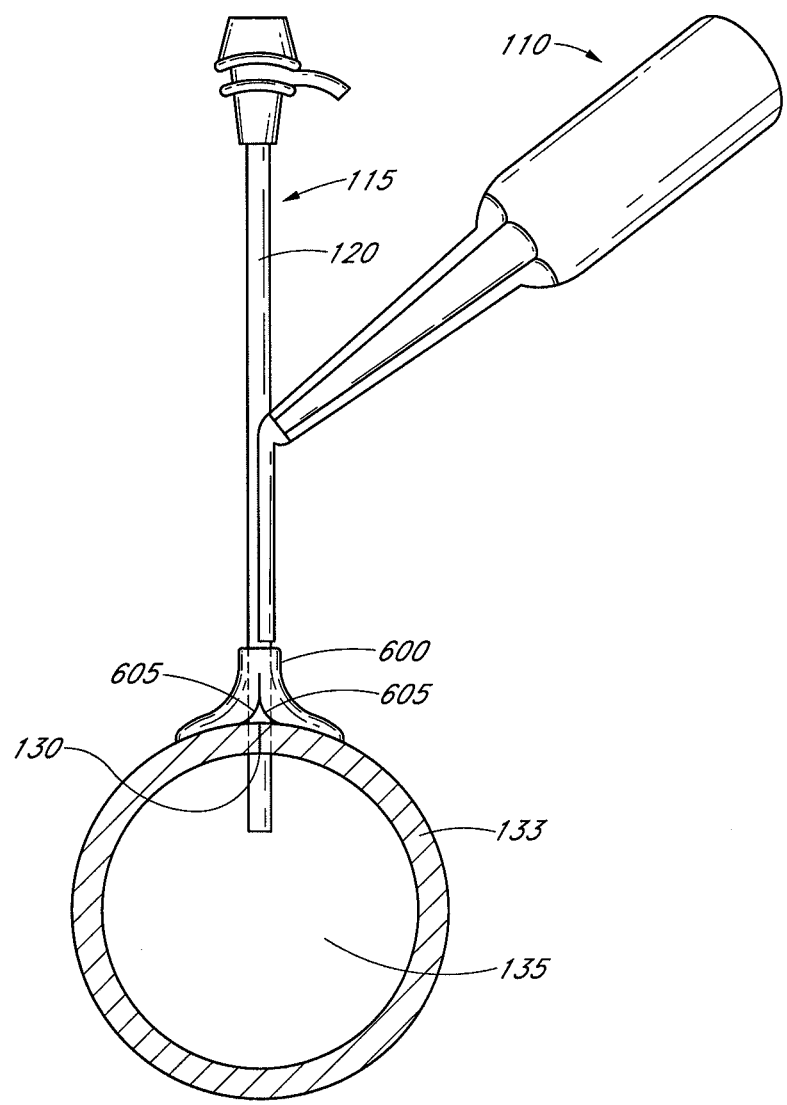

Referring to FIGS. 36 and 37, a ACD liner 500 includes a tube 505 that includes a radial slot 510 along an extending member 515 and through a first member 520 and a second member 525. The ACD inner liner 500 is sufficiently openable to be threaded onto the introducer from its side. Any configuration of the ACDs described herein can be built around the ACD liner 500 with a slot formed within the ACD. The tube 505 optionally can extend from the ACD and then be clamped at the proximal end once the ACD liner 500 and ACD are deployed.

Referring to FIGS. 38-41, a plug style ACD 550 that is similar to ACD 105 includes a channel 555 into which a deployment tool 552 is inserted to deploy the ACD through an arteriotomy to close the arteriotomy. The ACD includes an adhesive layer 560 for bonding to the tissue. The ACD 550 differs from the ACD 105 in that the channel 555 does not extend the entire length of the ACD. An ACD 570 (FIG. 39) is similar to the ACD 550 except that it has limited vessel protrusion, similar to the ACD 200 above. The ACD 550, 570 is placed into the arteriotomy and held briefly for an adhesive bond to form. The deployment device 552 then can be removed.

The distal end of the deployment tool 552 also can have a grasping feature to grasp the proximal end of the plug ACD during deployment and to release after the plug ACD has been seated in or is on the vessel, and able to release when the tool is being withdrawn.

Referring to FIGS. 42-45, an ACD can have a distal end geometry, which once positioned at the puncture site, is designed to compress the vessel wall for increased securement and sealing. For example, a ACD 600 may have a flare 605, or two or more longitudinal slits in the side of the tube, that are designed to open, or flare apart when advanced and in contact with the top of the vessel puncture site (i.e., arteriotomy). The ACD 600 can be made from a very elastic material and/or a superelastic/shape memory material such that when the introducer is removed, the flares or slits will pinch, or otherwise bring the edges of the punctured vessel together, effectively creating hemostasis. The inside of the flared section of the closure device could have biocompatible contact adhesive, other bonding material, and/or small barbs or protrusions that may assist in securing the device to the top of the vessel wall.

Figure 46:
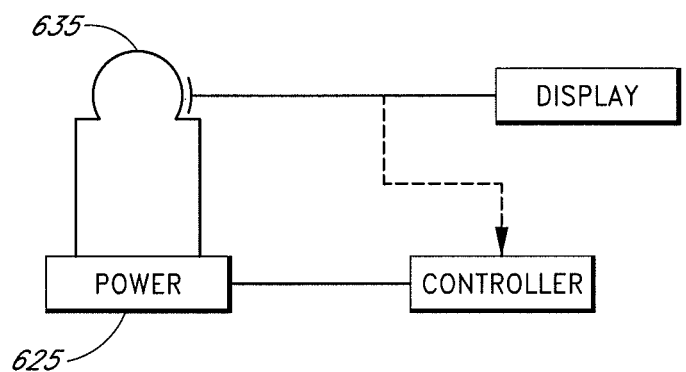
FIGS. 46 and 47 are electrical schematics for a direct resistive element heating circuit and an ohmic tissue heating circuit.
Figure 47:
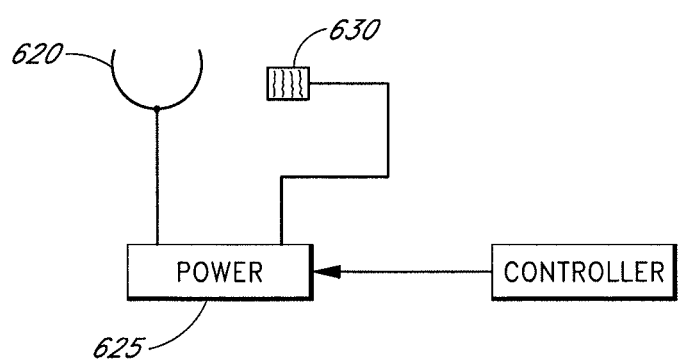
Figure 48:
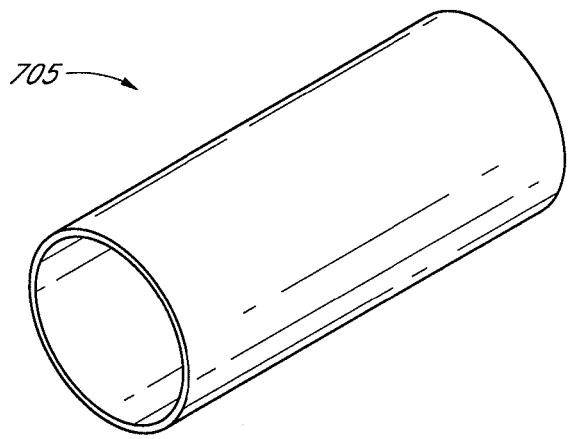
FIG. 48 is a perspective view of a tube used to fabricate a arterial closure device.
Figure 49:
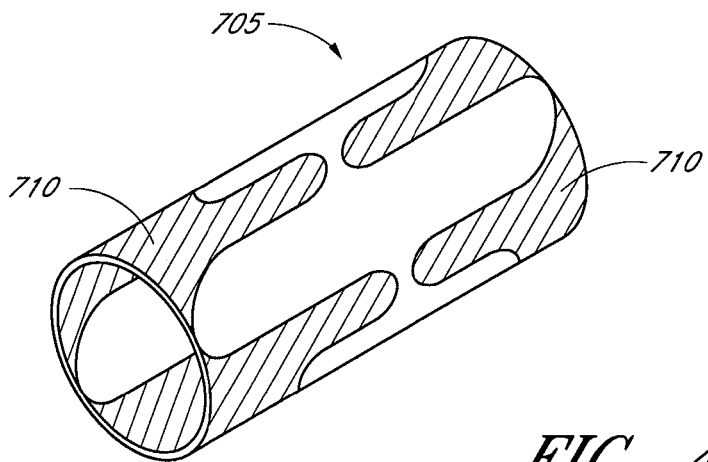
FIG. 49 is a perspective view of the tube of FIG. 48 showing material being removed.

Referring to FIGS. 46 and 47, heat can be used to assist with, or as an adjunct to, the process by recovering the ACD, activating (e.g., causing to flow, etc.) a hemostatic material to the puncture site that assists in sealing (e.g., through vessel contraction including the denaturing and reformation of collagen at the site) or accelerate healing, or a combination of these or other beneficial effects. Direct resistive element heating (FIG. 46) or ohmic tissue heating (FIG. 47) can be utilized. Biocompatible electrode materials (e.g., gold, platinum, and other suitable materials) can be mixed with the base material of the ACD as a powder during manufacturing, or as a wire, strip, or other geometry, added onto any surface of the device, and connected to a suitable (i.e., electrical and biocompatible) conductor. For ohmic tissue heating, one conductor 620 is connected to an RF power source. Another conductor is connected to a ground pad 630 placed on the patient's body, and also connected to the power source. For direct resistive element heating, both conductors from the power source 625 are connected to an electrode 635. Once the sealing of the puncture site has occurred, a twisting, cutting, or other manipulative action removes the conductor previously attached to the closure device. Alternatively, a special tip is placed over a standard electro surgical tool (e.g., Bovie) to insert through the skin and make contact with the closure device, tissue or both.

Alternative versions of the closure device may utilize an electrode that is formed by ion deposition, sputter coating, spraying, dip coating, adhesive, combination or other method or design.

Figure 50:
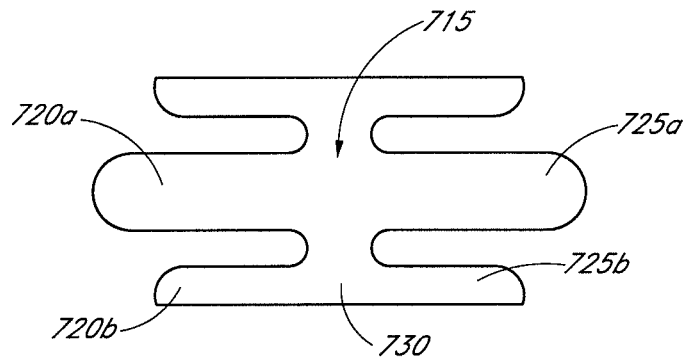
FIG. 50 is a side view of the tube of FIG. 48 with the material removed.
Figure 51:
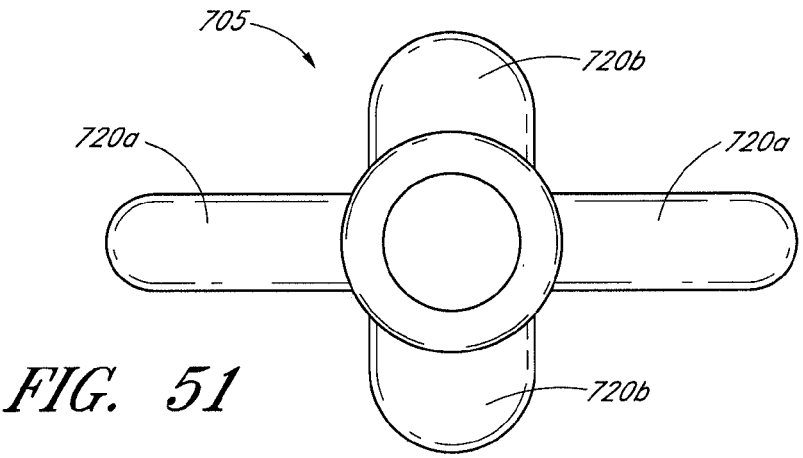
FIG. 51 is a top view of the curved configuration.
Figure 52:
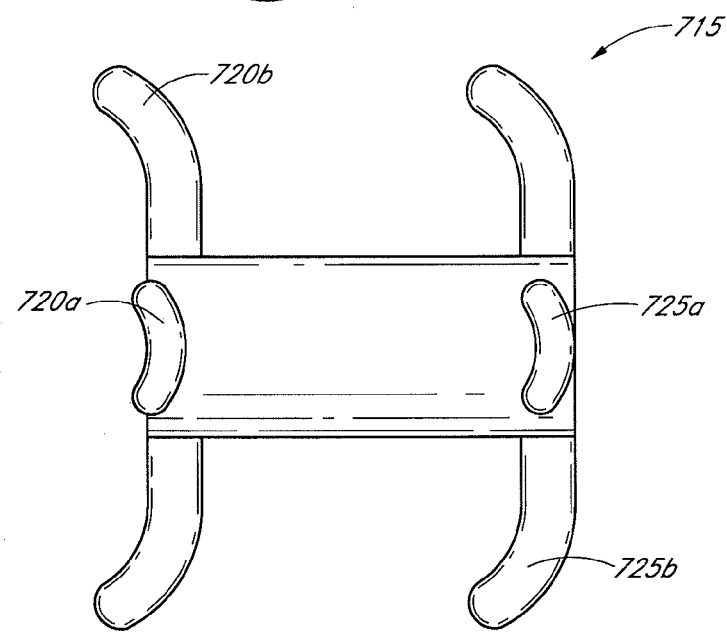
FIG. 52 is a side view of the configuration of FIG. 51.
Figure 53:
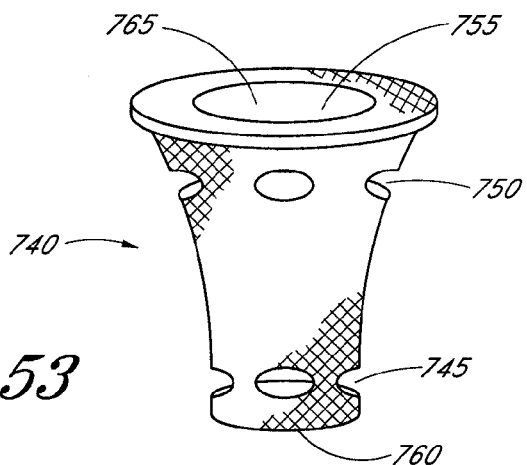
FIG. 53 is a perspective view of a fabric covering.

Referring to FIGS. 48-58, a superelastic/shape memory ACD 700 is made from a superelastic/shape memory sheet or tube 705. The sheet or tube 705 is etched, cut, or otherwise machined to remove material 710 (FIG. 49) to leave a starting configuration 715 (FIG. 50). The method of removing the material may be, for example, photo-etching and/or laser or chemical cutting. The starting configuration includes first extending members 720, second extending members 725, and a connecting member 730 between the first and second extending members. The first and second extending members 720 and 725 then are bent and curved (FIGS. 51 and 52). The first and second extending members are curved to mate with the inner and outer surface, respectively, of a vessel. For example, longer first and second extending members 720a and 725a are bent to be generally perpendicular to the connecting member 730 and have a curvature that is similar to that of the length dimension of a vessel wall. The shorter first and second extending members 720b and 725b are bent to have a radius of curvature that is similar to that of the radius of curvature of the circumference of a vessel wall. The shapes of the first and second extending members 720, 725 are set using known techniques of imparting shapes in superelastic/ shape memory materials, as described in further detail below.

Figure 54:
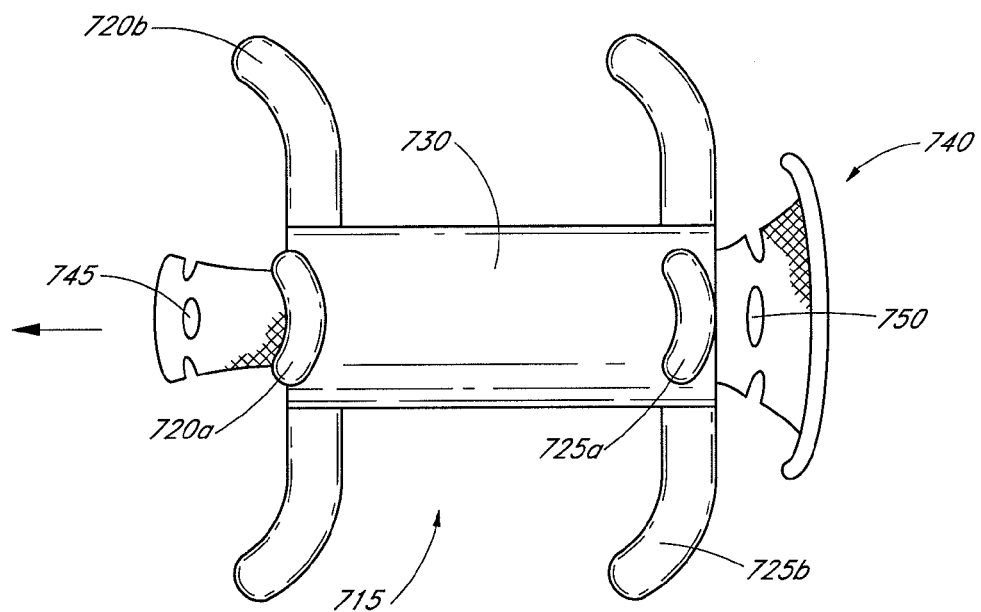
FIGS. 54-58 are side views showing the fabric covering of FIG. 53 being mounted within the curved configuration of FIG. 51 to form a arterial closure device.
Figure 55:
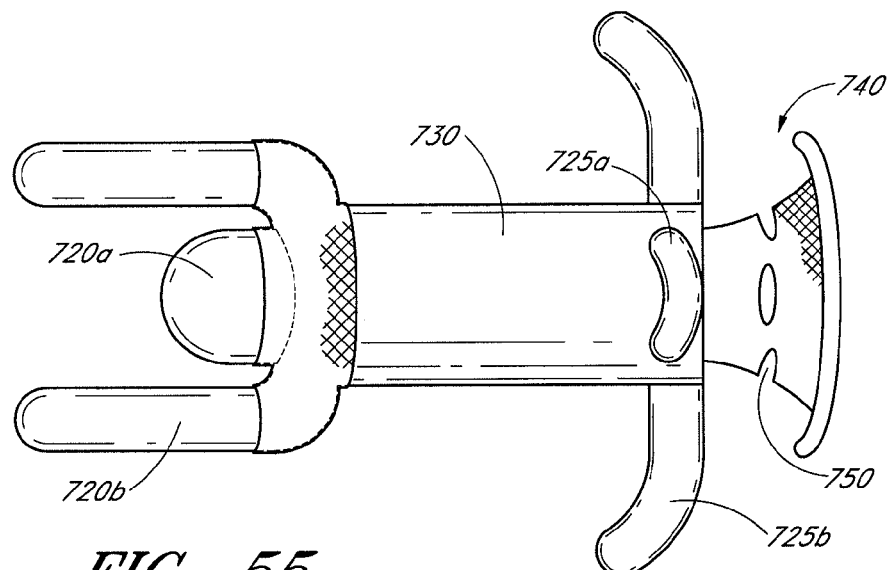
Figure 56:
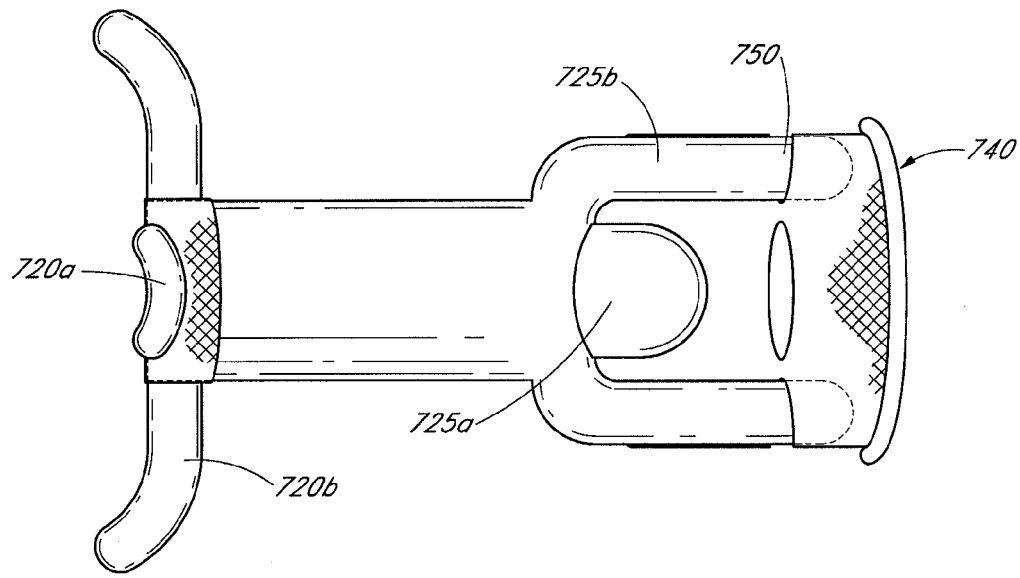
Figure 57:
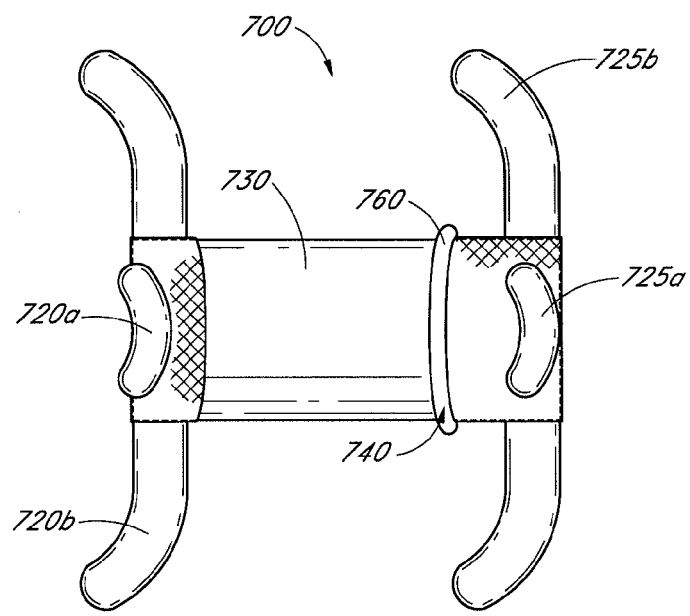
Figure 58:
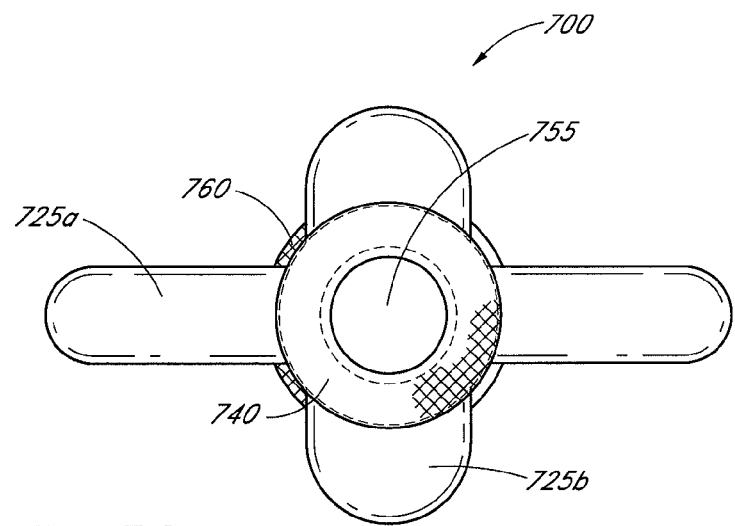

A fabric covering 740 (FIG. 53), such as Dacron, then is mounted to the curved configuration 715. The covering 740 includes distal side openings 745 and proximal side openings 750. A longitudinal channel 755 passes between a distal opening 760 and a proximal opening 765. The covering 740 is pulled distal end through the curved configuration 715 and the extending members 720 are straightened from their retracted state and passed through the distal side openings 745 (FIG. 54). The covering 740 then is pulled back such that the distal side openings 745 are tight against the first extending members 720 (FIG. 55). The first extending members 720 then are allowed to expand back to their retracted state. The second extending members 725 then are straightened from their retracted state and passed through the proximal side openings 750 (FIG. 56). The second extending members 725 then are allowed to expand back to their retracted state, thereby trapping a proximal end 760 of the covering against the connecting member 730 between the first and second extending members 720, 725 (FIGS. 57 and 58). The longitudinal channel 755 passes through the covering 740 and the shaped configuration 715.

Figure 59:
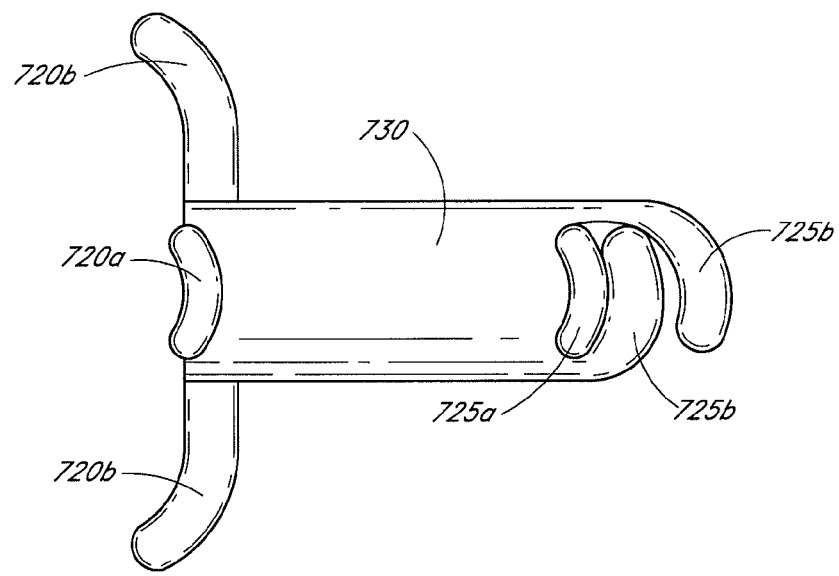
FIG. 59 is a side view of a configuration having side arms that fold over each other.

Referring to FIG. 59, the second extending members 725b can be configured to curve back over and under the opposite second extending member 725b. Thus, instead of curving against the outer circumference of the vessel in which the device is implanted, the second extending members 725b function to close the longitudinal channel 755 when they are in their retracted position. The covering 740 is mounted to the curved configuration 715 as described above. The second extending members 725b are kept in a straightened position because of the introducer or catheter that passes through the longitudinal channel 755. When the introducer or catheter is removed, the second extending members 725b return to their refracted position, thereby closing or partially closing the longitudinal channel 755. The covering 740 also contributes to the closure of the longitudinal channel 755 and reduction or elimination of blood leakage or seepage through the longitudinal channel.

Figures 60, 61:
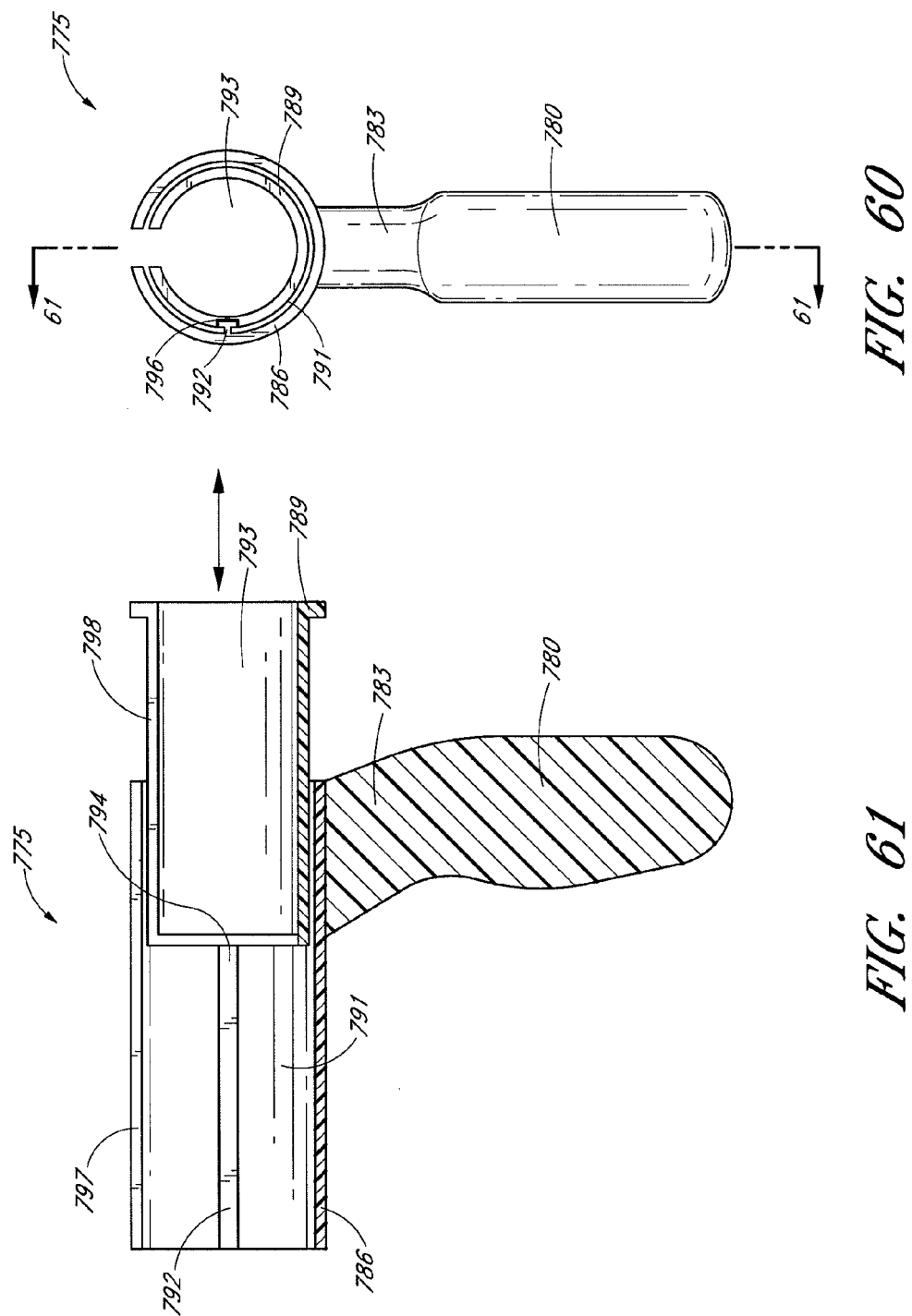
FIGS. 60 and 61 are front and cross-sectional side views of a deployment tool for deploying the arterial closure device.
Figure 62:
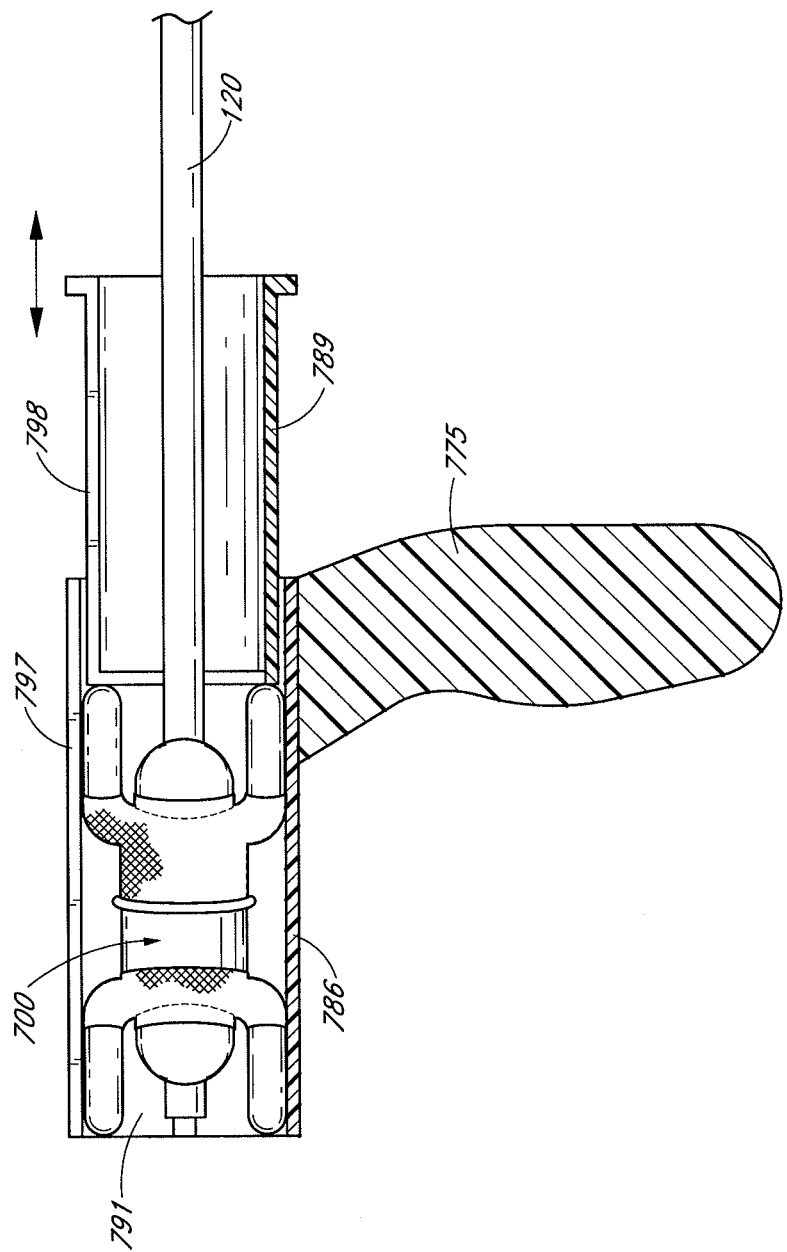
FIG. 62 is a cross-sectional side view of the deployment tool of FIG. 60 having the arterial closure device within.

Referring also to FIGS. 60-62, the ACD 700 is deployed using a deployment tool 775. The deployment tube includes a handle 780, an extension 783, a guide 786, and a pusher tuber 789. The guide 786 extends from the extension 783 and includes a first longitudinal channel 791 and a longitudinal ridge 792 that passes along the inner surface of the first longitudinal channel 791. The pusher tube 789 is slidably mounted within the first longitudinal channel 791 and includes a second longitudinal channel 793, a pusher surface 794, and a groove 796 that is configured to slide over the longitudinal ridge 792. The guide 786 and the pusher tube 789 include longitudinal slots 797, 798 so that the deployment tool 775 can be placed around the catheter or introducer. With the ACD 700 positioned over a catheter or introducer 120, and positioned within the longitudinal channel 791 in the guide 786, the physician pushes the ACD 700 along the introducer 120 into the vessel using the pusher tube 789. Of course, the ACD can be placed within an arteriotomy using other deployment tools or even by hand.

The ACDs herein may contain a metallic braid, coil, sheet, strip, wire, rod, or other configuration on the inner diameter, outer diameter, within, and/or a combination of these. The metallic material could be made from superelastic/shape memory alloys such as Nitinol. The metallic braid or coil could be annealed in one configuration during manufacture and processed and packaged in another configuration. When the material is exposed to normal body temperature (i.e., 37° C.), it will be set to either expand apart or contract inward depending on the design and annealed geometry (diameter). This characteristic may assist with the closure of the ACD.

It is important to understand basic terminology when describing metals with elastic, superelastic, or shape memory behavior. Elasticity is the ability of the metal, under a bending load, for example, to deflect (i.e., strain) and not take a permanent "set" when the load (i.e., stress) is removed. Common elastic metals can strain to about two percent before they set. Superelastic metals are unique in that they can withstand up to about ten percent strain before taking a set. This is attributed to a "stress-induced" phase change within the metal to allow it to withstand such dramatic levels of strain. Depending on the composition of the metal, this temperature that allows such a phase change can vary. And if the metal is "set" at one temperature, and then the temperature is changed, the metal can return to an "unset" shape. Then, upon returning to the previous "set" temperature, the shape changes back. This is a "shape-memory" effect due to the change in temperature changing the phase within the metal.

Elasticity is a key feature of superelastic materials. When a metal is loaded (i.e., stressed) and undergoes, for example, bending, it may deflect (i.e., strain) in a "springy" fashion and tend to return to its original shape when the load is removed, or it may tend to "set" and stay in a bent condition. This ability to return to the original shape is a measure of the elasticity or "resilience" of the metal. This ability for a metal to be resilient is desirable for such things as springs, shock absorbing devices, and even wire for orthodontic braces where the ability to deflect, but not deform (i.e., set) is important to maintain an applied force.

If, under a bending load, the metal takes a set, it is said to have plastically (versus elastically) deformed. This is because the imposed stress, produced by the bending load, has exceeded the "yield strength" (stress) of the metal. Technically, this level of stress that produces a set, is referred to as the "elastic limit", but is about the same as the yield strength. If the applied load increases past the yield strength of the metal, it will produce more plasticity and can eventually break. The higher the yield strength of the metal, the more elastic it is. "Good" elastic metals can accommodate up to about two percent strain prior to taking a set. But this is not the only factor governing "elasticity".

Another factor that determines the ability of a metal to deflect to a given, desired amount, but not take a set, is the "elastic modulus", or often called the modulus of elasticity. The modulus of the metal is an inherent property. Steels, for example, have a relatively high modulus (30 msi) while the more flexible aluminum has a lower modulus of about 10 msi. The modulus for titanium alloys is generally between 12 and 15 msi.

Resilience is the overall measure of elasticity or "spring-back ability" of a metal. The ratio of the yield strength divided by the modulus of the metal is the resilience. Although it is one thing for a metal to be resilient, it must also have sufficient strength for the intended service conditions.

As discussed above, when a metal is loaded, each increment of load (stress) produces a given increment of deflection (strain) within the metal. And the metal remains elastic if the applied is below the yield stress. However, there is a unique class of metal alloys that behave in an even more elastic manner. These are the "superelastic" metals, where, for a given applied stress (load) increment, the strain in the metal can reach 5 or 6 percent or more without taking a set. In these types of metals, the overall strain required to produce a set can reach an impressive 10 percent. This phenomenon is related to a phase change within the metal, and which is induced by the applied stress. This "stress-induced" phase change can also allow the metal to be set at one temperature and return to another shape at another temperature. This is a "shape-memory" effect, discussed below.

The most common superelastic metal, used in many commercial applications, is an alloy comprised of about equal parts of nickel (Ni) and titanium (Ti), and has a trade name of "Nitinol". It is also referred to as "NiTi". By slightly varying the ratios of the nickel and titanium in Nitinol, the stability of the internal phases in the metal can be changed. Basically, there are two phases: (1) an "austenite" phase and (2) a lower temperature, "martensite" phase. When the metal is in an austenitic phase condition and is stressed, then a stress-induced martensite forms, resulting in the super-elasticity. This is reversible, and the original shape returns upon release of the applied stress.

In general, the Ni-to-Ti ratio in the Nitinol is selected so that the stress-induced martensite forms at ambient temperatures for the case of super-elastic brace and support devices, which are used in ambient conditions. The specific composition can be selected to result in the desired temperature for the formation of the martensite phase (Ms) and the lower temperature (Mf) at which this transformation finishes. Both the Ms and Mf temperatures are below the temperature at which the austenite phase is stable (As and Af). The performance of an ACD can be further enhanced with the use of superelastic materials such as Nitinol. The superelasticity allows for greatly improved collapsibility, which will return to its intended original shape when the introducer (or catheter) is removed from the inside of the ACD. The high degree of flexibility is also more compatible with the stiffness of the engaged vessel.

By manipulating the composition of Nitinol, a variety of stress-induced superelastic properties can result, and over a desired, predetermined service temperature range. This allows the metal to behave in a "shape-memory" or "shape recovery" fashion. In this regard, the metal is "set" to a predetermined, desired shape at one temperature when in a martensitic condition, and which returns to the original shape when the temperature is returned to the austenitic temperature.

The shape memory phenomenon occurs from a reversible crystalline phase change between austenite and the lower-temperature martensite. In addition to this transformation occurring from an induced stress as described previously, it can, of course, also change with temperature variations. This transformation is reversible, but the temperatures at which these phase changes start and finish differs depending on whether it is heated or cooled. This difference is referred to as a hysteresis cycle. This cycle is characterized by the four temperatures mentioned previously, As, Af, Ms, and Mf. Upon heating from a lower-temperature martensite, the transformation to austenite begins at the As, and will be fully austenite at Af. And upon cooling, austenite will begin to transform back to martensite at the Ms temperature, and become fully martensitic at the Mf. Again, the specific composition of the alloy can result in a desired combination of these four transformation temperatures.

In the malleable martensitic state, the alloy can be easily deformed (set). Then upon heating back to the austenitic temperature, the alloy will freely recover back to its original shape. Then if cooled back to the martensitic state, the deformed shape reforms. The typical sequence of utilizing this shape memory property is to set the shape of, for example, a stent or anastomosis connector, while in the higher-temperature austenitic state. Then, when cooled, deform the martensite material, and then heat to recover the original shape.

Based on the background information provided above, it can be seen that if the Nitinol material requires an exceptionally tight bend, and one that would normally exceed the elastic limit of the material and thus permanently deform it, a bend can be placed in the device and the device annealed to relieve bending stresses within the device. Following this first bend, the device can be bent further to produce an even sharper bend, and then re-annealed to alleviate the stress from this additional bending. This process can be repeated to attain the desired, sharp bend or radii that would otherwise permanently deform the device if the bend were attempted in a single bending event. The process for recovery from the position of the most recent bend is then performed as described above.

Although the example of Nitinol, discussed above, is, by far the most popular of the superelastic metals, there are other alloys that can also exhibit superelastic or shape memory behavior. These include the following:
Copper-40 at % Zinc
Copper-14 wt % Aluminum-4 wt % Nickel
Iron-32 wt % Manganese-6 wt % Silicon
Gold-5 to 50 at % Cadmium
Nickel-36 to 38 at % Aluminum
Iron-25 at % Platinum
Titanium-40 at % Nickel-10 at % Copper
Manganese-5 to 35 at % Copper
Titanium-49 to 51 at % Nickel (Nitinol)

Nitinol, because of the large amount of titanium in the composition, has been the only FDA approved superelastic/shape memory alloy for medical implant devices. The corrosion resistance of Nitinol is superior to that of commonly used 3161 stainless steel, and, if surface oxidized or passivated carefully, can reach corrosion resistance comparable to the most popular titanium implant alloy, Ti6Al4V. Similarly, the metal piece can be electropolished to improve its biocompatibility and blood compatibility. Biocompatibility studies have routinely showed Nitinol as a metal with suitable biocompatibility for medical device applications.

In summary, there are various ways of describing elasticity, but the main criterion is the ability of the metal to return to its initial, pre-loaded shape. Some metals can only deflect a couple percent and remain elastic while others, such as superelastic Nitinol, can deflect up to about ten percent. Nitinol is also biocompatible and corrosion resistant. This unique combination of properties allows a device made of Nitinol, such as an arterial closure device, to be fully collapsed within a deployment tool and be subsequently released, at a particular site within the vessel, to form its intended service shape.

Materials other than superelastic/shape memory alloys may be used as reinforcements provided they can be elastically deformed within the temperature, stress, and strain parameters required to maximize the elastic restoring force thereby enabling the tubular closure device to recover to a specific diameter and/or geometry once deployed inside, over, or on top of the vessel or other location. Such materials include other shape memory alloys, spring stainless steel 17-7, other spring metal alloys such as Elgiloy™, Inconel™, superelastic polymers, etc.

When thermally forming superelastic/shape memory reinforcements, the superelastic/shape memory material(s), previously cut into the desired pattern and/or length, are stressed into the desired resting configuration over a mandrel or other forming fixture having the desired resting shape of the tubular plug, depending on the vessel size or other location where the ACD or plug is intended to be used, and the material is heated to between 300 and 650° Celsius for a period of time, typically between 30 seconds and 30 minutes. Once the volume of superelastic material reaches the desired temperature, the superelastic material is quenched by inserting into chilled water or other fluid, or otherwise allowed to return to ambient temperature. As such, the superelastic reinforcements are fabricated into their resting configuration. The superelastic/shape memory reinforcements may be full or partial length or width of the ACD or tubular plug.

Any metal or metal alloy, such as a superelastic/shape memory alloy that comes in contact with blood and/or tissue can be electropolished. Electropolishing may reduce platelet adhesion causing thrombosis, and encourage endothelization of the exposed metallic areas. Electropolishing also beneficially removes or reduces flash and other artifacts from the fabrication of the device.

Superelastic/shape memory materials, such as tubular, rectangular, wire, braid, flat, round, combination or other structures also can be used in the design of the closure device, to assist with grasping, contacting, bringing tissue together, sealing, or other desired function. When used as a hollow conduit or reinforcement to a conduit, the superelastic/shape memory materials could be used to resist compressive closure and act as a flexible reinforcing strain relief to prevent kinking and to prevent the conduit from closing.

Numerous modifications and/or additions to the above-described embodiments and implementations are readily apparent to one skilled in the art. It is intended that the scope of the present embodiments and implementations extend to all such modifications and/or additions and that the scope of the present embodiments and implementations is limited solely by the claims.

For example, the engagement/contact section of the deployment tool can have a cross sectional geometry of a complete circle that may be designed to split away from the introducer once the closure device has been advanced/deployed. Splitting could be accomplished by having thinned or weakened areas in the wall of the deployment device tubing, such as linear perforations, or linear scores, combination, or other perforation configuration. This version would require that the deployment tool be back loaded onto the introducer before the closure device is placed onto the introducer and prior to insertion into the vessel.

The deployment tool can be a clip-on tool, can compress the device to reduce the cross sectional profile prior to insertion and/or may include a constraining sheath to reduce a section, or sections of the device during insertion to the target site. This version would be particularly useful for bringing two tissue walls together while yet providing a conduit between the tissues.

The proximal end of the ACDs described herein may be closed using hemostats, or other tools, by pinching the end together until the inner diameter bonds, or compresses together. Adhesive may be used to assist in the closure of the device.

The proximal edge of the closure device and the distal (or other) edge of the advancement/deployment tool can have interlocking geometries to aid control during advancement (particularly when inserting by twisting or turning while advancing into the vessel).

The proximal edge or end of the closure device may have a collar made of a superelastic/shape memory material, an elastic combination of materials or suitable elastic materials that would compress the end of the device together once the introducer is removed from the inner diameter of the closure device. As previously mentioned, the closing and sealing of the device may be enhanced with an adhesive, swellable material, or other coating or layer.

The closure means can be other than a tubular structure, such as a plug. A special introducer, having multi-lumens, one for the catheter or other device, and at least one for the hemostatic plug material. The hemostatic material, and matching geometry plunger would be inserted into the proximal end of the special introducer. As the plunger is advanced, the hemostatic material is advanced into position and the introducer is withdrawn from the vessel.

The basic device, system and method can be sized and configured for medical devices other than vascular introducers, such as guide wires, catheters, laparoscope, endoscope, trocar, cannula, electrode wire, or other.

Using the tubular closure device, especially when made from swellable material, as a reversible sterilization method for women by occluding the fallopian tubes, and men by occluding the vas ducts or tubes.

A modified version of the device and system can be used for the closure of septal defects in the heart, as well as anywhere else in the body. For this, as well as other additional applications, the clip on section of the deployment tool would be modified to fit onto the catheter, and be long enough (such as, e.g., full catheter length) to be remotely advanced from the proximal end of the catheter. The deployment tool also may be modified and used to compress the device during insertion into the body to thereby reduce the cross-sectional profile during insertion. The deployment method may be enabled by longitudinal movement, manipulation, or retraction of the deployment tool away from the closure device, which removes the compression of the device and allows the device to expand and fill in the opening, such as a septal defect.

The ACDs described herein can be used for cardiovascular applications where hemostasis (temporary or permanent) is desired. Additionally, the ACDs can be used with simple modifications for any tubular, duct, organ, hollow body cavity, or other structures or tissues, where temporary or permanent sealing or plugging is needed, or alternatively, where a conduit or conduit reinforcement is desired. For conduit or conduit reinforcement applications, the material and design used thereby would be sufficiently resistant to compressive closure while still remaining flexible, e.g., longitudinally and/or radially flexible.

The ACDs described herein also can be used for gastric bypass procedures, general tissue bunching or bringing tissues together, and on or in other vessels, organs, tissues, bones, and/or other body tissues than those specifically described.

While several particular forms of the arterial closure device and deployment tool have been illustrated and described, it will be apparent that various modifications and combinations of the inventions detailed in the text and drawings can be made without departing from the spirit and scope of the inventions. For example, references to materials of construction, methods of construction, specific dimensions, shapes, utilities or applications are also not intended to be limiting in any manner and other materials and dimensions could be substituted and remain within the spirit and scope of the inventions. Accordingly, it is not intended that the inventions be limited, except as by the appended claims. Accordingly, other embodiments are within the scope of the following claims and figures.

What is claimed is:

1. A tissue closure device for delivery into an opening in a blood vessel wall using a plunger and a medical device, the tissue closure device consisting of:
- a proximal end configured to coupled with a distal end of the plunger during advancement of the tissue closure device;
- a distal end;
- an elongate non-tapered surface with a solid core between the proximal end and the distal end;
- a first radially extending element extending radially outward from the surface positioned at the distal end of the tissue closure device, the first radially extending element comprising a proximal surface; and
- a second radially extending element extending radially outward from the surface positioned between the distal end and the proximal end of the tissue closure device, the second radially extending element comprising a distal surface;
- wherein the first and second radially extending elements are at least partially compressible, deformable or deflectable to have a first configuration when positioned within the medical device and a second configuration when advanced beyond a distal end of the medical device,
- wherein the proximal surface of the first radially extending element is adapted to contact and conform to an inner surface of the blood vessel wall near the blood vessel wall opening when the radially extending element is in the second configuration, and
- wherein the distal surface of the second radially extending element is adapted to contact and conform to an outer surface of the blood vessel wall near the blood vessel wall opening when the radially extending element is in the second configuration,
- wherein the tissue closure device is formed from a single piece.

2. The tissue closure device of claim 1 wherein the elongate non-tapered surface with the solid core has a cross-sectional geometry selected from the group comprising round, oval, elliptical, triangular, rectangular, square, ridged, x-shaped, star-shaped, cross-shaped, and combinations thereof.

3. The tissue closure device of claim 1, wherein the medical device is selected from the group comprising at least one of an introducer, a needle, a catheter, an endoscope, a trocar, a cannula, and an electrode wire.

4. The tissue closure device of claim 1, wherein the closure device is deliverable through an introducer sheath.

5. The tissue closure device of claim 1, wherein the closure device has a first diameter along a first portion of its length and at least a second diameter along a second portion of its length.

6. The tissue closure device of claim 1, wherein at least one of the proximal end or the distal end is flared.

7. The tissue closure device of claim 1, wherein the first radially extending element extends further from the surface than the second radially extending element.

8. The tissue closure device of claim 1, wherein the portion of the tissue closure device between the proximal end and the distal end is solid.

9. The tissue closure device of claim 1, wherein the tissue closure device has an hourglass shape.

10. The tissue closure device of claim 9, wherein the hourglass shape is adapted to seat the tissue closure device within the tissue opening.

11. The tissue closure device of claim 10, wherein the tissue closure device has a small diameter section bordered by two larger diameter sections and further wherein a distance is provided longitudinally between a first larger diameter section and a second larger diameter section.

12. The tissue closure device of claim 1, wherein the tissue closure device has a cross-sectional geometry selected from the group comprising: oval, elliptical, rectangular, square, ridged, triangle, x-shaped, star-shaped, cross-shaped, and combinations thereof.

13. The tissue closure device of claim 1, wherein the tissue closure device is made from a material that is at least one of biocompatable, bioabsorbable, swellable, and biodegradable.

14. The tissue closure device of claim 13, wherein the material is one or more material selected from the group comprising: collagen, cellulose, hydrogels, polyglycolide, polyglycolic acid, polylactic acid, starch, polymer, polyethylene polymer, lactide, and caprolactone.

15. The tissue closure device of claim 13, wherein the material is swellable in the presence of fluid.

16. The tissue closure device of claim 15, wherein the fluid is selected from the group comprising blood, saline and subcutaneous fluid.

17. The tissue closure device of claim 1, wherein the tissue closure device is made from one or more materials that are bioabsorbable.

18. The tissue closure device of claim 1, wherein the tissue closure device is removable from the blood vessel wall opening.

19. The tissue closure device of claim 1, wherein the tissue closure device is manufactured in part from a radiopaque material.

20. The tissue closure device of claim 1, wherein the tissue closure device is configured to include a tissue engagement area.

21. The tissue closure device of claim 1, wherein the tissue closure device is adapted to deliver a therapeutic or an adhesive agent to at or near the tissue opening.

22. The tissue closure device of claim 1, wherein the tissue closure device is adapted to temporarily or permanently cinch, anchor, close, compress, seal, stabilize, reduce an open space for tissue or reinforce tissue.

23. The tissue closure device of claim 1, wherein the tissue closure device is configured to be used with the medical device.

24. The tissue closure device of claim 23, wherein the medical device is selected from the group comprising at least one of an introducer, a needle, a catheter, an endoscope, a trocar, a cannula, and an electrode wire.

25. The tissue closure device of claim 1 wherein the first radially extending element and the second radially extending element are deflected proximately when positioned within the medical device, and are expanded when advanced beyond the distal end of the medical device.

26. The tissue closure device of claim 25, wherein the first radially extending element and the second radially extending element are configured to contact and conform to a tissue surface when in the expanded state.

27. The tissue closure device of claim 26 wherein the tissue surface is an artery.

28. The tissue closure device of claim 1 wherein the surface with the solid core does not extend distally past the first radially extending element positioned at the distal end of the tissue closure device.

29. The tissue closure device of claim 28 wherein the second radially extending element is a continuous piece.

30. The tissue closure device of claim 1 wherein first radially extending element positioned at the distal end has a different geometry than the second radially extending element between the distal end and the proximal end.

31. The tissue closure device of claim 1 wherein the tissue closure device is removable from the tissue opening.

* * * * *